(12) United States Patent
Yi et al.

(10) Patent No.: US 10,639,229 B2
(45) Date of Patent: May 5, 2020

(54) THREE-DIMENSIONAL NEGATIVE PRESSURE STIMULATOR MODULE CAPABLE OF PERFORMING CUSTOMIZED COMPOSITE STIMULATION FOR IMPROVEMENT OF SKIN FUNCTIONS

(71) Applicants: SD BIOTECHNOLOGIES CO., LTD., Seoul (KR); TAEYI LIFESCIENCE INC., Yongin-si, Gyeonggi-do (KR)

(72) Inventors: Tae-Hoo Yi, Seoul (KR); Chang-shik Yin, Seongnam-si (KR); Seuk-Hwan Chung, Suwon-si (KR); Sul-Woong Park, Seoul (KR)

(73) Assignees: SD BIOTECHNOLOGIES CO., LTD., Seoul (KR); TAEYI LIFESCIENCE INC., Yongin-si, Gyeonggi-Do (KR)

( * ) Notice: Subject to any disclaimer, the term of this patent is extended or adjusted under 35 U.S.C. 154(b) by 749 days.

(21) Appl. No.: 15/227,021

(22) Filed: Aug. 3, 2016

(65) Prior Publication Data
US 2017/0056281 A1 Mar. 2, 2017

(30) Foreign Application Priority Data
Aug. 31, 2015 (KR) .................. 10-2015-0123090

(51) Int. Cl.
*A61H 9/00* (2006.01)
*A61N 5/06* (2006.01)
(Continued)

(52) U.S. Cl.
CPC ......... *A61H 9/0057* (2013.01); *A61N 5/0616* (2013.01); *A61N 5/0625* (2013.01);
(Continued)

(58) Field of Classification Search
CPC .. A61H 9/0057; A61H 23/00; A61H 2230/50; A61H 2230/65;
(Continued)

(56) References Cited

U.S. PATENT DOCUMENTS 6,042,537 A * 3/2000 Kaiser .................... A61H 9/005
600/38
2004/0236252 A1* 11/2004 Muzzi .................. A61B 18/203
601/1

(Continued)

FOREIGN PATENT DOCUMENTS

KR 10-2001-0056675 A 7/2001
KR 10-0561333 B1 3/2006
(Continued)

*Primary Examiner* — Quang D Thanh
*Assistant Examiner* — Matthew R Moon
(74) *Attorney, Agent, or Firm* — Novick, Kim & Lee, PLLC; Jae Youn Kim

(57) ABSTRACT

The present invention relates to a three-dimensional negative pressure stimulator module capable of performing customized composite stimulation for the improvement of skin functions that applies three-dimensional negative pressure stimulation as well as composite stimulation such as electric current stimulation, light stimulation, and thermal stimulation, which is helpful in improving functions of the skin, to skin compositively, and further has a function of sensing a skin state, thereby performing customized composite stimulation. The three-dimensional composite stimulator module includes: a negative pressure cup; and at least one diaphragm provided along the transmission path of the negative pressure of the negative pressure cup, wherein at least any one of negative pressure stimulation, light stimulation, thermal stimulation, and electrical stimulation is transmitted compositively to the skin or subcutaneous tissues.

6 Claims, 26 Drawing Sheets

(51) Int. Cl.
*A61N 1/32* (2006.01)
*A61N 5/067* (2006.01)
*A61F 7/00* (2006.01)
*A61N 1/36* (2006.01)
*A61N 1/04* (2006.01)

(52) U.S. Cl.
CPC ............. *A61F 2007/0071* (2013.01); *A61H 2201/0207* (2013.01); *A61H 2201/0228* (2013.01); *A61H 2201/0235* (2013.01); *A61H 2201/10* (2013.01); *A61H 2201/1207* (2013.01); *A61H 2201/5005* (2013.01); *A61H 2201/5007* (2013.01); *A61H 2201/5071* (2013.01); *A61H 2201/5082* (2013.01); *A61H 2230/25* (2013.01); *A61H 2230/50* (2013.01); *A61H 2230/65* (2013.01); *A61N 1/0408* (2013.01); *A61N 1/328* (2013.01); *A61N 1/36014* (2013.01); *A61N 2005/067* (2013.01); *A61N 2005/0651* (2013.01)

(58) Field of Classification Search
CPC .... A61H 2201/0207; A61H 2201/0228; A61H 2201/0235; A61H 2201/10; A61H 2201/1207; A61H 2201/50; A61H 2201/5005; A61H 2201/5007; A61H 2201/5071; A61H 2201/5082; A61H 2201/5092; A61F 2007/0071; A61N 5/0616; A61N 5/0625; A61N 1/36014; A61N 1/0408; A61N 1/328; A61N 2005/067; A61N 2005/0651
See application file for complete search history.

(56) References Cited

U.S. PATENT DOCUMENTS

| | | | | |
|---|---|---|---|---|
| 2006/0259102 | A1* | 11/2006 | Slatkine | A61B 17/205 607/88 |
| 2007/0027411 | A1* | 2/2007 | Ella | A61H 7/008 601/7 |
| 2008/0106896 | A1* | 5/2008 | Liu | A61H 9/0057 362/234 |
| 2011/0112520 | A1* | 5/2011 | Michael | A61B 18/14 606/13 |
| 2012/0150079 | A1* | 6/2012 | Rosenberg | A61H 7/003 601/6 |
| 2012/0253416 | A1* | 10/2012 | Erez | A61H 9/0057 607/3 |
| 2015/0057578 | A1* | 2/2015 | Min | A61H 9/0057 601/6 |
| 2015/0283022 | A1* | 10/2015 | Lee | A61F 7/007 601/2 |
| 2016/0128605 | A1* | 5/2016 | Moreno | A61B 5/0531 600/547 |
| 2016/0128894 | A1* | 5/2016 | Horton | A61H 9/0057 601/11 |
| 2018/0133499 | A1* | 5/2018 | Dronov | A61N 1/403 |

FOREIGN PATENT DOCUMENTS

| | | | | |
|---|---|---|---|---|
| KR | 100913842 B1 * | 8/2009 | ......... | A61H 9/0057 |
| KR | 10-1042837 B1 | 6/2011 | | |
| KR | 10-1089737 B1 | 12/2011 | | |
| KR | 10-2013-0053099 A | 5/2013 | | |
| KR | 20-0472454 Y1 | 4/2014 | | |

* cited by examiner

THREE-DIMENSIONAL NEGATIVE PRESSURE STIMULATOR MODULE CAPABLE OF PERFORMING CUSTOMIZED COMPOSITE STIMULATION FOR IMPROVEMENT OF SKIN FUNCTIONS

CROSS-REFERENCE TO RELATED APPLICATIONS

This application claims the benefit of priority under 35 USC 119(a) of Korean Patent Application No. 10-2015-0123090 filed on Aug. 31, 2015, in the Korean Intellectual Property Office, the entire disclosure of which is incorporated herein by reference for all purposes.

BACKGROUND OF THE INVENTION

Field of the Invention

The present invention relates to a three-dimensional negative pressure stimulator module capable of performing customized composite stimulation for improvement of skin functions, and more particularly, to a three-dimensional negative pressure stimulator module capable of performing customized composite stimulation for improvement of skin functions by applying three-dimensional negative pressure stimulation as well as composite stimulation such as electric current stimulation, light stimulation, and thermal stimulation, which stimulations' parameters may be optimized for improvement of targeted skin functions, and by providing functions of sensors on the skin state, thereby performing the customized composite stimulation.

Background of the Related Art

As the skin is aged, the arrangements and density of collagen fibers are changed, and particularly, collagen type 1 on dermis is arranged in the direction parallel to the surface of the skin, while showing the decrement in the interaction between water and collagen. Characteristics of photoaged skin are related with the damages and degradations of collagen fibers and elastin fibers. The elasticity of skin is decreased due to the reduction of the collegan fibers and the elastic fibers. In young people, thin collegan fibers are distributed at a high density, and in old people, contrarily, thick collegan fibers are distributed sparsely. This is known as a mechanism of wrinkle formation.

If the wrinkle is properly treated, it is expected that the number of the collagen fibers and elastin fibers are increased, the skin elasticity is improved, and the number of wrinkles is reduced. For example, a long pulsed 1064 nm Nd:YAG laser (LPND) that may be generated from a non-invasive medical device is known to penetrate deep into the skin, with expected effect of increase in the number of the collagen fibers and elastin fibers. Further, IPL (Intense Pulsed Light) irradiation is known to induce enlargement of collagen fibers, with resultant improvement of skin function anti-wrinkle effects. When negative pressure is applied to the skin as a modality of skin stimulation with appropriate intensity for an appropriate period of time, the volume of skin is expanded and the fibers of the skin are partially rearranged reflecting both the external negative pressure and the elastic characteristics of the skin itself. Especially, negative pressure stimulation and other simulations such as light irradiation (LED, IPL, or the like) and others may be combined and optimized for faster and more efficient regeneration of the collagen fibers in the skin than individual stimulations. Combined and optimized stimulation may be used for such skin conditions as acne vulgans, vascular lesion, pigmentation, hair follicle problems, impaction of foreign matter in sebaceous glands, skin wrinkles, and so on.

Cosmetic devices for wrinkle improvement suggested and developed in conventional practices are largely classified into (1) a simple stimulation device which may conduct, for example, galvanic stimulation through the flow of micro current, and (2) a composite stimulation device which applies a combination of, for example, light stimulation, vibration stimulation, and negative pressure stimulation to skin, at the same time. According to the existing devices of negative pressure stimulation, however, the degree and shape of skin deformation under negative pressure stimulation cannot be controlled effectively. Only the maximum degree of the skin deformation under maximum degree of negative pressure may be controlled and the shape of skin deformation is usually of flat elevation or of oval elevation of the skin. Three-dimensional rearrangements and diverse ways of expansion of the elastin fibers are not applied to the skin. Therefore, such expected effects as improved skin function and improvement in the skin wrinkles are usually limited. Further, if the stimulation of negative pressure is not effectively controlled within an appropriate limit, problems like hyperpigmentation may occur. Since the negative pressure stimulation is also used for the management of skin conditions, there is a need for development of a new stimulation device that may solve the above-mentioned problems occurring in the conventional devices, while applying optimal stimulation.

On the other hand, one of conventional composite stimulation methods including negative pressure stimulation is disclosed (in Korean Patent Application Laid-open No. 10-2013-0053099, which is entitled 'smart cupping treatment device'), wherein a diaphragm made of an elastic film, which closes the opening of a cup structure, is brought into contact with the skin, and then, the elastic film itself is heated so as to apply thermal stimulation to the skin. However, the negative pressure and heat may not be transmitted effectively to the skin due to the characteristics and structure of the diaphragm. Further, a soft elastic material should be used as a diaphragm to secure its elasticity to transmit the negative pressure to the skin. Besides, it is easily expected that the soft elastic diaphragm may turn defective due to repeated applications, only to lose its functionality as a transmitter of the negative pressure and heat stimulation. The elastic film and accompanying parts may be repeatedly exchanged with new ones. In addition, even if the negative pressure is monitored by a sensor to adjust the degree of negative pressure, individual difference in the tensile characteristics and elasticity characteristics of the skin may result in different degrees of deformation of the skin and subcutaneous tissues under the same negative pressure. The degree of deformation of skin and subcutaneous tissues may not be effectively controlled within safe and intended range. Unexpected adverse results such as venous bleeding, hyperpigmentation, excessive stimulation may follows.

In addition, another conventional composite stimulation method including negative pressure stimulation is disclosed (in Korean Patent Registration No. 10-1042837, which is entitled 'portable cupping device having laser diode'), wherein a supportive pillar-like is equipped inside a cutting cup structure and maintained in the state where the central area of the cupping device is brought into premature contact with the skin due to the supportive pillar like part during negative pressure stimulation period. In other words, the supportive pillar-like part limits the efficacy of negative pressure stimulation for the central area of the cupping device. When the skin and tissues around the skin are deformed by the negative pressure in the cupping cup structure upon the application of negative pressure stimulation, the degree of deformation of the skin and tissues is substantially restricted by means of the formation of the support member, thus reducing the negative pressure stimulation effects.

Further, one of conventional light stimulation devices for the improvement of the skin using LED elements is disclosed (in Korean Utility Model Registration No. 20-0472454, which is entitled 'easily portable treatment machine for skin improvement using LED'), wherein one LED chip or two or more LED chips selected from five LED chips as an LED part for emitting one of visible light, near-infrared rays, and far-infrared rays is (are) located to provide a portable LED machine for treatment. However, other types of stimulation such as electrical current stimulation, and negative pressure stimulation cannot be applied to the skin compositively.

Furthermore, still another conventional composite stimulation device including negative pressure stimulation is disclosed (in Korean Patent Registration No. 10-1089737, which is entitled 'negative pressure and radio-frequency generation type composite handset') to apply deep-heating stimulation accompanied by negative pressure stimulation and radio-frequency stimulation, wherein radio-frequency catheters are located to a shape of a circle along the skin contact surface of a cupping cup. In this case, the treatment region of the negative pressure is the large contact surface of the skin to which the cupping cup is applied. However, the treatment region of the radio-frequency stimulation is just the periphery of the large contact surface of the skin to which the cupping cup is applied. That is, the stimulation to the large contact surface where the treatment is deemed necessary is not a composite stimulation of the negative pressure and the radio-frequency. The composite stimulation is only applied to the peripheral rim area of the cupping cup, which may result in the limitation of the effects that may be expected from the composite stimulation.

In case of the composite stimulation device, particularly, the whole circular portion inside the opening of the cupping cup is a region to be stimulated, but electrical or magnetic stimulation is applied just to the very small periphery of the cupping cup, thus failing to apply the composite stimulation to the whole region where the negative pressure stimulation is applied. Further, electrical or magnetic stimulation elements are located only on a narrow peripheral rim of a circle along the skin contact surface of the opening of the cupping cup, so that if the skin contact surface is small, an impedance resistance is increased on the skin contact surface, thus making it hard to effectively transmit the electrical or magnetic stimulation to the skin.

As mentioned above, there have been proposed conventional composite stimulation devices for applying the negative pressure stimulation compositively with one or more of the electrical stimulation, the light stimulation, and the thermal stimulation. However, the negative pressure of those conventional devices is evenly applied to the large contact area and lacks dynamic change in its form over the stimulated skin area. Furthermore, even if they apply the composite stimulation such as electrical stimulation, light stimulation, and thermal stimulation, the area of composite stimulation is limitedly to a small region.

SUMMARY OF THE INVENTION

Accordingly, the present invention has been made in view of the above-mentioned problems occurring in the prior art, and it is an object of the present invention to provide a three-dimensional negative pressure stimulator module capable of performing customized composite stimulation for improving skin functions wherein various three-dimensional deformation of the skin is induced in a three-dimensional space when skin and subcutaneous tissues are deformed and rearranged by negative pressure, thus applying optimized negative pressure stimulation for the intended effects on the skin like improvement of the wrinkle, which is of course different from the existing simple negative pressure stimulation. In addition, the intensity of the negative pressure is adjusted over the time, thus effectively controlling the three-dimensional rearrangements of the skin and subcutaneous tissues over the time. Furthermore, composite stimulation with light, heat and electrical stimulation is applied to the large skin area to which the negative pressure stimulation is applied. Precise and continuous monitoring of the state of the skin is performed by sensors during the stimulation period, thereby the composite stimulation may be customized and individualized.

To accomplish the above-mentioned object, according to the present invention, there is provided a three-dimensional negative pressure stimulator module capable of performing customized composite stimulation for improving skin functions, the module including: a negative pressure cup; and at least one diaphragm provided along negative pressure transmission paths of the negative pressure cup, wherein one or more of negative pressure stimulation, light stimulation, thermal stimulation, and electrical stimulation are transmitted compositively to the skin or subcutaneous tissues.

According to the present invention, preferably, the negative pressure transmission paths are paths for flowing air from the lower portion of the negative pressure cup toward the upper portion thereof, so that the air inside the negative pressure cup is discharged therethrough to apply the negative pressure stimulation to the skin below the cupping cup.

According to the present invention, preferably, one or more of the diaphragms are disposed along the negative pressure transmission paths. When two or more of the diaphragms are disposed, there are the first diaphragm and the second diaphragm, where the first diaphragm comes into contact with a target region of the skin or being nearest thereto and the second diaphragm spaced apart from the first diaphragm by a given distance in a vertical direction or in up and down direction in such a manner as to have no contact with the target region of the skin during the period when the negative pressure is applied.

According to the present invention, preferably, while the open end of the cupping cup in tight contact with the skin, the first diaphragm is semispherical, concave, convex, or flat in shape on the whole thereof to physically limit the maximum degree of deformation of the target region of the skin by negative pressure, so that the skin deformedly protrudes toward the concave side of the first diaphragm and comes into contact with the first diaphragm when deformed maximally.

According to the present invention, preferably, the whole shape of the second diaphragm is any one selected from semispherical, concave, convex, and flat shapes.

According to the present invention, preferably, the first diaphragm and the second diaphragm have a circular or polygonal sectional shape, and a whole or partial surface of the skin contact surface of the first diaphragm has at least any one form of a saw tooth, a cylinder, a pulse, and a wave so as to physically limit and shape the maximum degree of deformation of the target region of the skin by the negative pressure.

According to the present invention, preferably, the first diaphragm has an edge area enlarged to locate at least one of stimulation elements for stimulating the target region of the skin and sensing elements for sensing the state of the target region of the skin.

According to the present invention, preferably, the first diaphragm is provided integrally with the negative pressure cup at the inside of the negative pressure cup or separable from the negative pressure cup, so that in case of the integral structure, the first diaphragm is adjusted in position vertically or up and down to control the maximum degree of deformation of the target region of the skin by the negative pressure, and in case of the separable structure, the first diaphragm is located selectively to block or allow the air flows to effectively transmit the negative pressure.

According to the present invention, preferably, the first diaphragm and the second diaphragm have vents formed on a partial or the whole region of the surface thereof in such a manner as to pass air therethrough and thus to form the negative pressure.

According to the present invention, preferably, the vents have at least one of shapes such as a line, a circle, a polygon, a character, a symbol, and a plate.

According to the present invention, preferably, the first diaphragm has concave and convex elements formed thereon to three-dimensionally shape the deformation of the target region of the skin to a previously set degree when the negative pressure stimulation is applied, so that the target region of the skin is deformed, expanded, or rearranged spatially by means of the concave and convex elements and thus subjected to the negative pressure stimulation.

According to the present invention, preferably, the concave and convex elements have at least any one form selected from a cylinder, a sphere, a square pyramid, and a triangular pyramid, so that partial deformation of the target region of the skin is adjusted to an intended degree.

According to the present invention, preferably, the first diaphragm or the second diaphragm has the stimulation elements for applying stimulation to the target region of the skin or the sensing elements for sensing the state of the target region of the skin.

According to the present invention, preferably, the vents serve as paths through which the stimulation generated from the stimulation elements reach directly the target region of the skin or serve as paths through which the state of the target region of the skin is sensed, and higher negative pressure stimulation through the region where the vents are formed is applied to the target region of the skin.

According to the present invention, preferably, the first diaphragm and the second diaphragm have the stimulation elements and the sensing elements disposed alone or in combination of two or more elements, the stimulation elements being at least one selected from an electrical stimulation element, a light stimulation LED element, a thermal stimulation element, and a laser element, and the sensing elements being at least one selected from a temperature sensor, an impedance sensor, a blood flow sensor, and a pressure sensor.

According to the present invention, preferably, the three-dimensional composite stimulator module further includes a controller for controlling the intensity of the negative pressure according to the time and controlling the other stimulation elements and the sensing elements.

According to the present invention, preferably, both of the temporal three-dimensional stimulation through the controller and the spatial three-dimensional stimulation through the concave and convex elements are applied to the target region of the skin.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENTS

Figure 1:
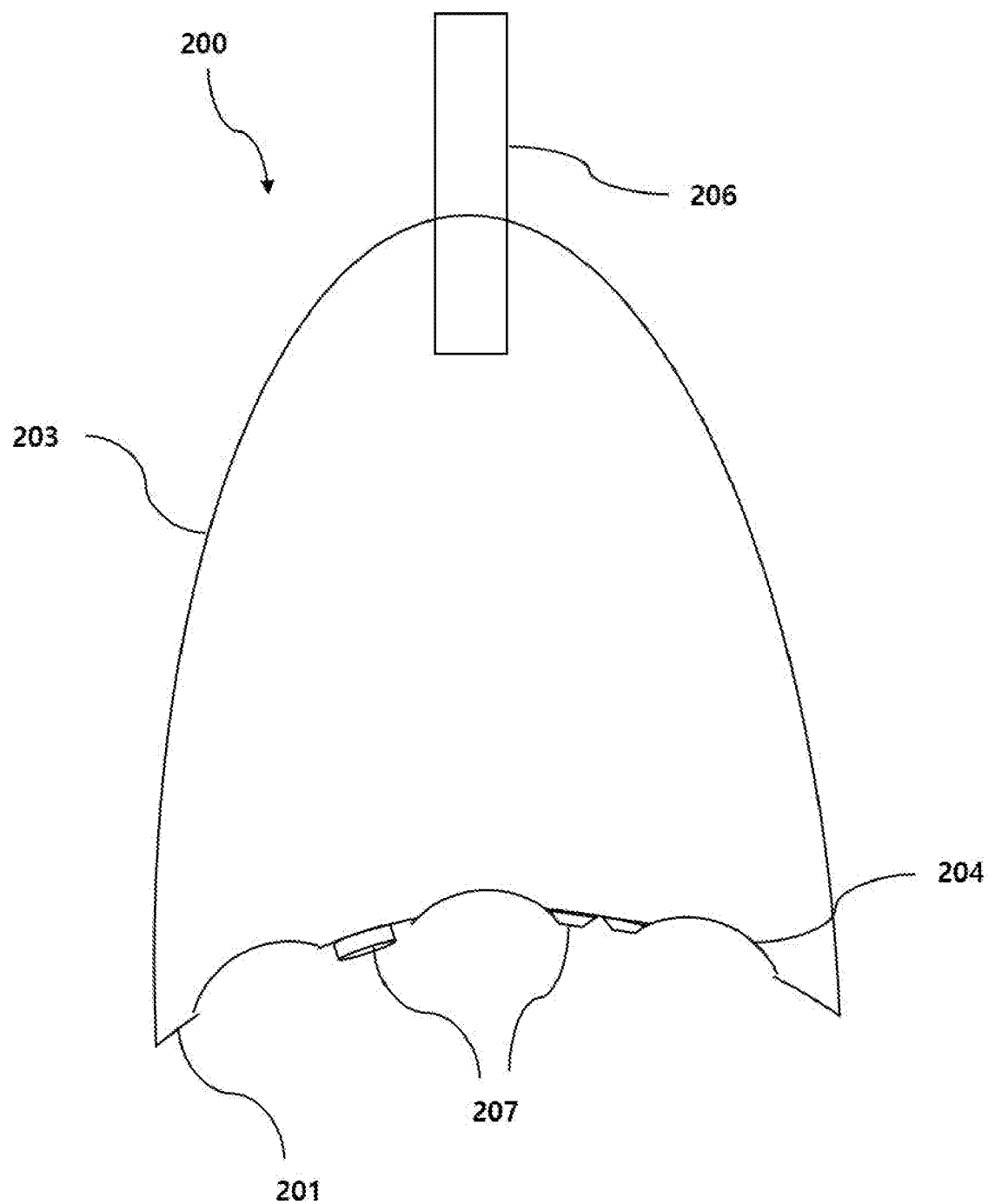
FIG. 1 shows a basic structure of a negative pressure cup according to the present invention, wherein the negative pressure cup is configured to have a single diaphragm.

Hereinafter, an explanation on a three-dimensional negative pressure stimulator module capable of performing customized composite stimulation for improving skin functions according to the present invention will be given in detail with reference to the attached drawing. Before the present invention is disclosed and described, it is to be understood that the disclosed embodiments are merely exemplary of the current invention, which can be embodied in various forms. Therefore, specific structural and functional details disclosed herein are not to be interpreted as limiting, but merely as a basis for the claims and as a representative basis for teaching one of ordinary skills in the art to variously employ the present invention in virtually any appropriately detailed structure.

According to the present invention, there is provided a three-dimensional negative pressure stimulator module capable of performing customized composite stimulation for improving skin functions (hereinafter, referred to as 'three-dimensional composite stimulator module'), which is a cosmetic and medical device that applies three-dimensional negative pressure stimulation as well as composite stimulation such as electric current stimulation, light stimulation, and thermal stimulation, which is helpful in improving the skin functions, to the skin compositively, and further has a function of sensing the state of the skin, thereby performing an optimized and individualized stimulation to the skin.

According to the present invention, a three-dimensional composite stimulator 10, which has a concave single or multiple diaphragm structures, applies three-dimensional negative pressure stimulation through composite concave and convex elements and vents formed along a concave semispherical surface of the first diaphragm 201 as a surface close to the skin, and diaphragms of a negative pressure cup 200 effectively transmit negative pressure to the first diaphragm 201 as the surface close to the skin through their respective vents, collectively or distributedly. Further, stimulation elements and sensing elements are disposed supportedly against the diaphragms. Beyond the simple negative pressure stimulation, accordingly, multi-dimensional composite stimulation such as three-dimensional negative pressure stimulation, micro current stimulation, light stimulation, thermal stimulation and so on, which effectively changes the three-dimensional arrangements of the skin or subcutaneous tissues, is applied stably over a large area, and the state of the skin is monitored through the sensing elements including an impedance sensor, a temperature sensor, a blood flow sensor, a pressure sensor and the like to optimize the composite stimulation to the current state of an individual's skin state, thus effectively achieving the expected effects in skin care. Hereinafter, an explanation on the three-dimensional composite stimulator module according to the present invention will be given in detail with reference to the attached drawing.

(Diaphragm Structure)

Figure 2:
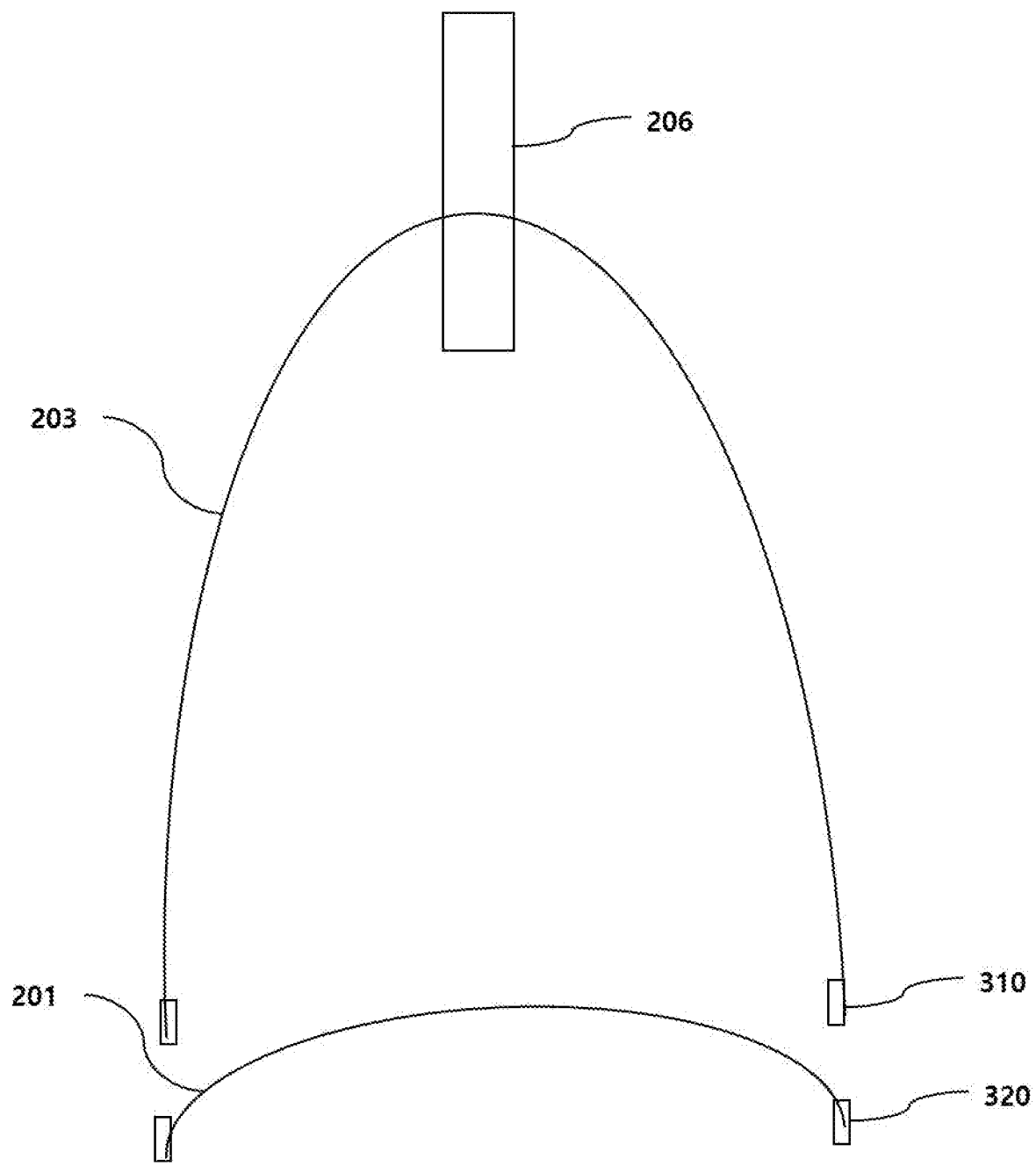
FIG. 2 shows a separation structure of the first diaphragm of the negative pressure cup according to the present invention.
Figure 3:
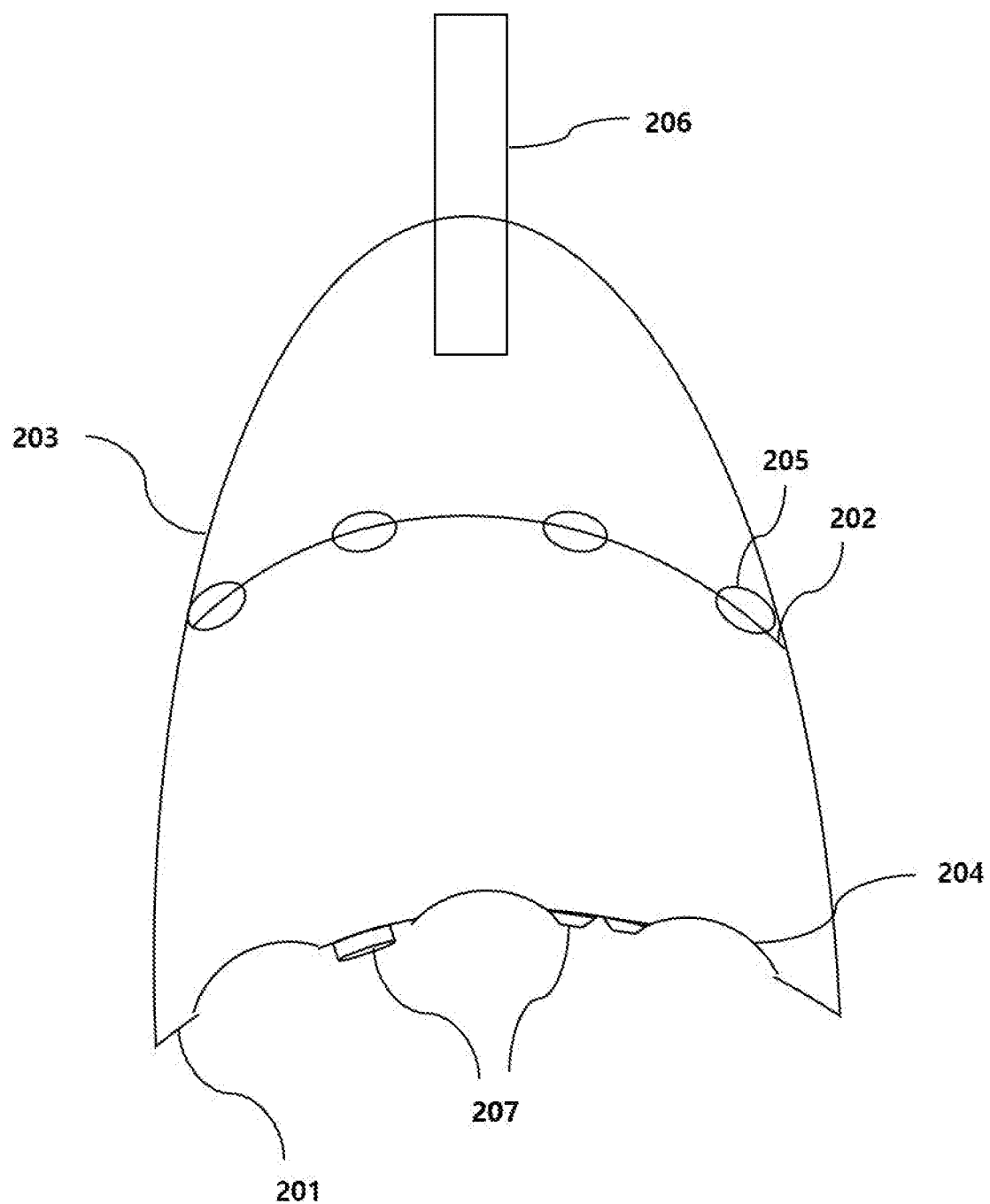
FIG. 3 shows a basic structure of a negative pressure cup according to the present invention, wherein the negative pressure cup is configured to have multiple diaphragms.

As shown in FIG. 1, the three-dimensional composite stimulator module according to the present invention is provided with the negative pressure cup 200. The negative pressure cup 200 is classified into a cupping cup and a suction cup, but it is not limited thereto. Only if stimulators apply stimulation to the skin by means of negative pressure, they may be within the technological scope of the present invention. As shown in FIG. 1, the negative pressure cup 200 according to the present invention largely includes the first diaphragm 201 and the third diaphragm 203. The third diaphragm 203 is a housing or body of the negative pressure cup 200 and semispherical or concave on a whole shape thereof. Hereinafter, accordingly, the third diaphragm 203 is called a housing. The first diaphragm 201 is located inside the housing 203 and is semispherical or concave on a whole shape thereof. According to another example, as shown in FIG. 2, the first diaphragm 201 is separable from the housing 203. Additionally, as shown in FIG. 3, the second diaphragm 202 is located above the first diaphragm 201 and is semispherical, concave, convex, or flat on a whole shape thereof. If necessary, accordingly, additional diaphragms may be located above the second diaphragm 202 or between the first diaphragm 201 and the second diaphragm 202 inside the housing 203. At this time, if the negative pressure cup 200 is provided with the first diaphragm 201 and the housing 203, it has a single diaphragm structure, and if the negative pressure cup 200 is provided with the first diaphragm 201, the second diaphragm 202, and the housing 203, it has a multiple diaphragm structure. The housing 203, the first diaphragm 201 and the second diaphragm 202 are made of a metal material (hard or semi-hard material) like stainless steel. However, the first diaphragm 201 is brought into direct contact with skin, and therefore, it may be made of a soft material, not hard material, if desirable. If the first diaphragm 201 is semispherical, advantageously, it produces negative pressure, effectively comes into contact with the skin, and applies a variety of three-dimensional negative pressure stimulation to the skin.

Figure 4:
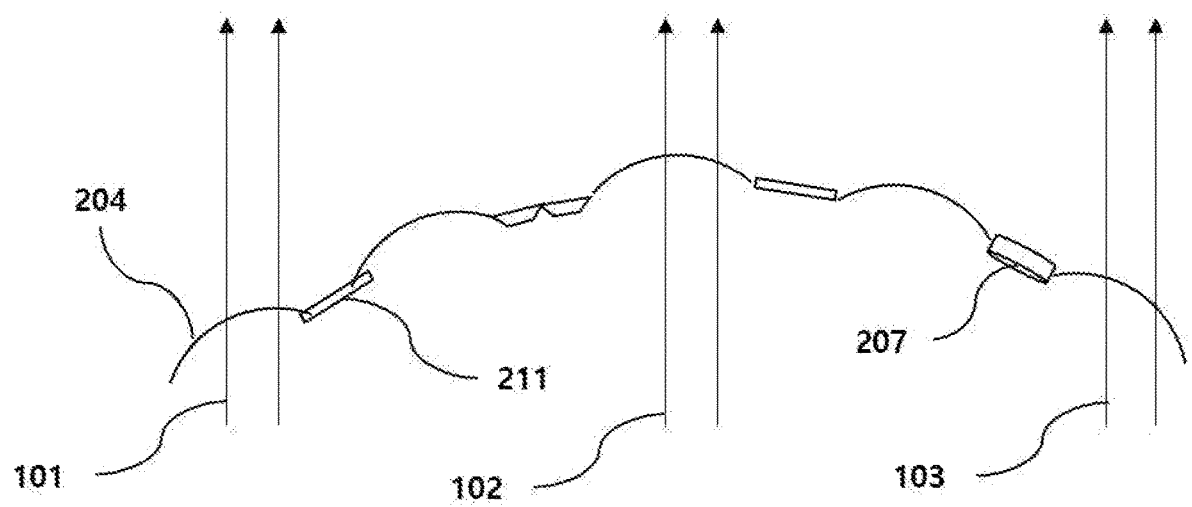
FIG. 4 shows air flows (or negative pressure transmission paths) in the negative pressure cup according to the present invention.

FIG. 1 is a bottom view showing the semispherical first diaphragm 201 providing a skin contact surface. The first diaphragm 201 is located along the transmitting path of the negative pressure to a target region (for example, the skin or subcutaneous tissues, which will be referred to as the skin), for example, on the intermediate paths of air flows 101, 102 and 103 as shown in FIG. 4. Further, the first diaphragm 201 includes vents 204 and concave and convex elements 207 adapted to effectively change the three-dimensional shape of the skin. Each diaphragm in the single diaphragm structure or in the multiple diaphragm structure has the vents 204, 205 and 206 formed as air flow ventilation holes (or air holes, or vents), and the first diaphragm 201 further includes the concave and convex elements 207. If necessary, the first diaphragm 201 includes stimulation elements 210 or sensing elements 230, without having the concave and convex elements 207. However, the first diaphragm 201 desirably includes the concave and convex elements 207 so as to effectively change the three-dimensional shape of the skin when the negative pressure is applied to the skin. The first diaphragm 201 and the second diaphragm 202 have the vents 204 and 205 having various sizes, shapes, formation positions and numbers thereof, and the first diaphragm 201 has the concave and convex elements 207 having various sizes, shapes, formation positions and numbers thereof on the skin contact surface thereof.

FIG. 1 shows a basic structure of the negative pressure cup 200 according to the present invention. The first vents 204 and the concave and convex elements 207 are formed on the first diaphragm 201 contacted with the skin or close to the skin. When the negative pressure stimulation is applied to the skin through the first vents 204, the skin comes into close contact with the concave surface of the first diaphragm 201 and the concave and convex elements 207 formed on the surface of the first diaphragm 201, and the first vents 204 are the points at which the negative pressure is transmitted additionally to the skin contact surface of the first diaphragm 201. That is, the negative pressure transmitted from the region above the first diaphragm 201 is strongly transmitted directly to the skin around the vents 204 (direct transmission), and the negative pressure transmitted through the vents 204 is indirectly transmitted to the skin contact surface of the first diaphragm 201 (indirect transmission).

Further, the negative pressure is applied collectively and distributedly to the first diaphragm 201 through the first vents 204, thus transmitting the negative pressure stimulation to the skin. That is, as shown in FIGS. 8 to 11, the formation positions of the vents 204 are different, thus allowing the negative pressure stimulation to be collected to any one skin region or distributed over the whole skin region.

The first diaphragm 201 and the second diaphragm 202 are semispherically formed inside the housing 203. Particularly, the first diaphragm 201 prevents the skin from being deformed excessively when the negative pressure stimulation is applied to the skin (See FIG. 20b). That is, the first diaphragm 201 has the semispherical shape in such a manner as to control the distance from the skin to the first, thus preventing any excessive deformation of the skin, and accordingly, the skin is physically limitedly deformed and protrudes (limited degree of the maximum deformation) only within the optimal range previously set according to the degree of concavity of the first diaphragm 201 and the surface shape (for example, a saw tooth or wave shape) of the first diaphragm 201. Therefore, the skin is deformed and protrudes only within the limited range of deformation offered by the semispherical structure and surface shape of the first diaphragm 201, thus evading such risk that the skin and subcutaneous tissues are excessively deformed and adverse reactions like venous bleeding occur when the negative pressure stimulation to the skin is excessive as is often the case of conventional practice, as shown in FIG. 20a.

Figure 20A:
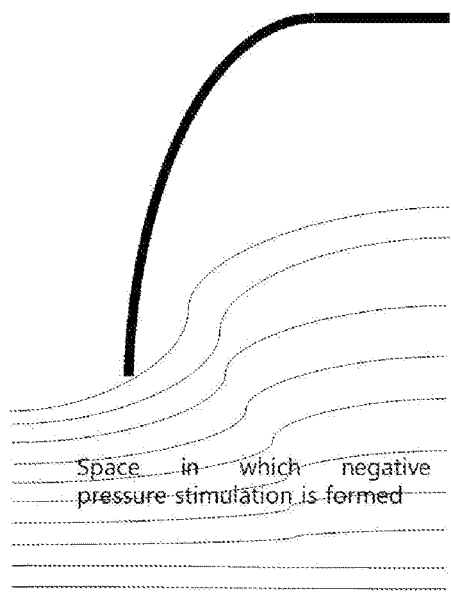
FIG. 20a is a schematic figure showing the deformation and three-dimensional rearrangements of the skin and subcutaneous tissues under the negative pressure stimulation in the conventional practice.

Under the conventional negative pressure stimulator as shown in FIG. 20a, the whole deformation of the skin and subcutaneous tissues caused by the negative pressure stimulation is not effectively controlled, with inevitable risk of adverse reactions like post-inflammatory hyperpigmentation. If the negative pressure stimulation is applied excessively, further, the deformation of the skin and subcutaneous tissues is also induced excessively, so that the skin and subcutaneous tissues may be congested or bleed.

Figure 20B:
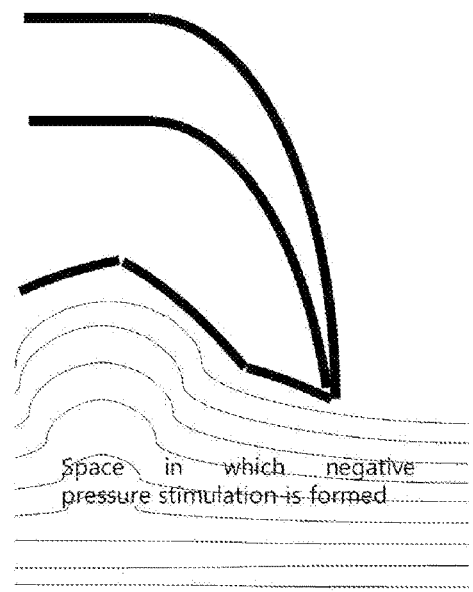
FIG. 20b is a schematic figure showing the deformation and three-dimensional rearrangements of the skin and subcutaneous tissues under the negative pressure stimulation according to the present invention.

Under the negative pressure cup 200 according to the present invention as shown in FIG. 20b, contrarily, even if the negative pressure stimulation is applied to the maximum, the maximum degree of deformation of the skin is effectively controlled within the limit of the concave shape of the first diaphragm 201 and the surface shape thereof, thus putting aside any risk as in the conventional practice. Further, the first diaphragm 201 and the second diaphragm 202 serve as supports to the concave and convex elements 207, the stimulation elements 210, and the sensing elements 230 as will be discussed later. Accordingly, the negative pressure stimulation is applied to the skin having the same area as the first diaphragm 201. According to the present invention, the concave and convex elements 207 having various shapes are located along the surface of the first diaphragm 201, and then, the vents 204 are formed therealong, so that when the skin and subcutaneous tissues are expanded or rearranged in a three-dimensional space, the three-dimensional stimulation is applied spatially. Further, the intensity of the negative pressure stimulation is continuously controlled through a controller 430 as will be discussed later throughout the period of stimulation, thus applying three-dimensional negative pressure stimulation temporally. That is, the three-dimensional deformation of the skin and subcutaneous tissues and resultant rearrangement of the tissues is effectively controlled to apply optimized stimulation to various targets such as keratin, melanocyte, collagen, elastin fibers, hair follicles, sweat glands, blood vessels, lymph, and nerves, which are stimulated through the deformation of the tissues thereof, thus advantageously achieving the expected effects in the skin. In addition to the spatial control of the negative pressure intensity through the controller 430, furthermore, the state of the skin is continuously monitored by the sensing elements, and the information on the current state of the skin is transmitted to the controller 430, so that the negative pressure stimulation can be effectively controlled and optimized by the controller 430.

Figure 21:
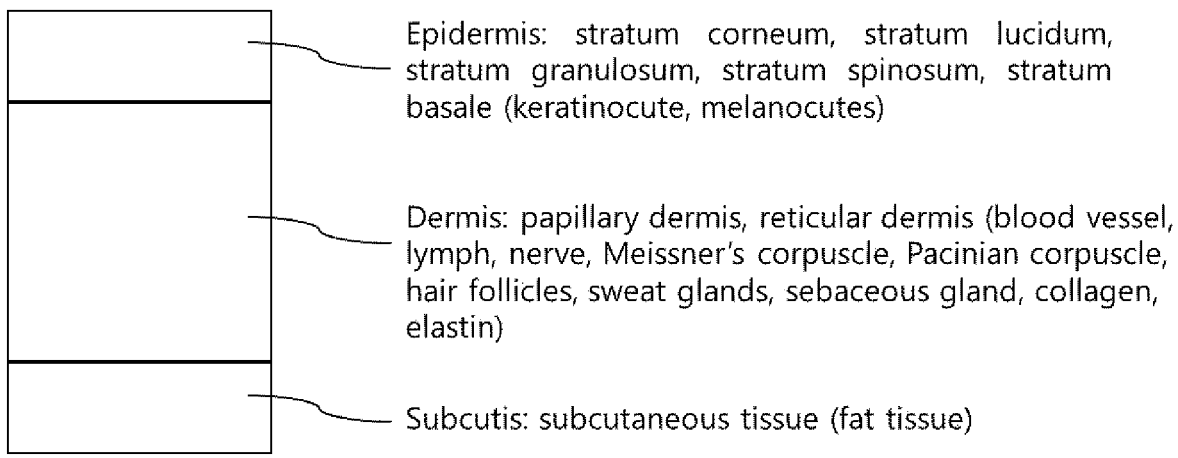
FIG. 21 shows a diagram of the skin and subcutaneous tissues that are the therapeutic targets of the present invention.

When the negative pressure stimulation is applied, the skin coming into contact with the first diaphragm 201 is deformed in such a manner as to be brought into complete or almost complete contact with the first diaphragm 201. At this time, higher intensity stimulation of negative pressure is applied to the skin area facing the vents 204, and the deformation of the skin is controlled variously according to the shapes of the three-dimensional concave and convex elements 207 located along the surface of the first diaphragm 201, thus allowing the deformation and rearrangements of the skin tissues to be formed variously. Accordingly, diverse stimulations such as three-dimensional deformation, expansion, or rearrangement of the tissues are applied spatially to the components (See FIG. 21) of the skin and subcutaneous tissues such as collagen, elastin fibers, and so on. Also, the intensity of the negative pressure stimulation is controlled through the controller 430 during the period of negative pressure stimulation, and accordingly, the three-dimensional structure of the skin and subcutaneous tissues such as collagen, elastin fibers, and so on are effectively stimulated during the period of negative pressure stimulation. As a result, the negative pressure stimulation is effectively applied to prevent any adhesions or atrophy of the collagen and elastin fibers. Further, sensory receptors like Meissner's corpuscle, Pacinian corpuscle, and so on are stimulated through the tissue deformation thereof. In addition, hair follicles, sweat glands, sebaceous glands, blood vessels, lymph, nerves, keratin cells, melanocyte, and fat cells are effectively stimulated by three-dimensional deformation and re-arrangement.

The suction device or cupping device in the conventional practice applies just a simple negative pressure stimulation to the skin. According to the present invention, however, the three-dimensional stimulation is applied spatially by means of the formation of the overall shape of the diaphragm 201, the concave and convex elements 207 having various shapes, and the vents 204 formed on the surface of the first diaphragm 201, and further, it is applied temporally by means of the controller 430, thus effectively achieving the stimulation of three-dimensional rearrangement of the components of the skin and subcutaneous tissues.

Figure 7:
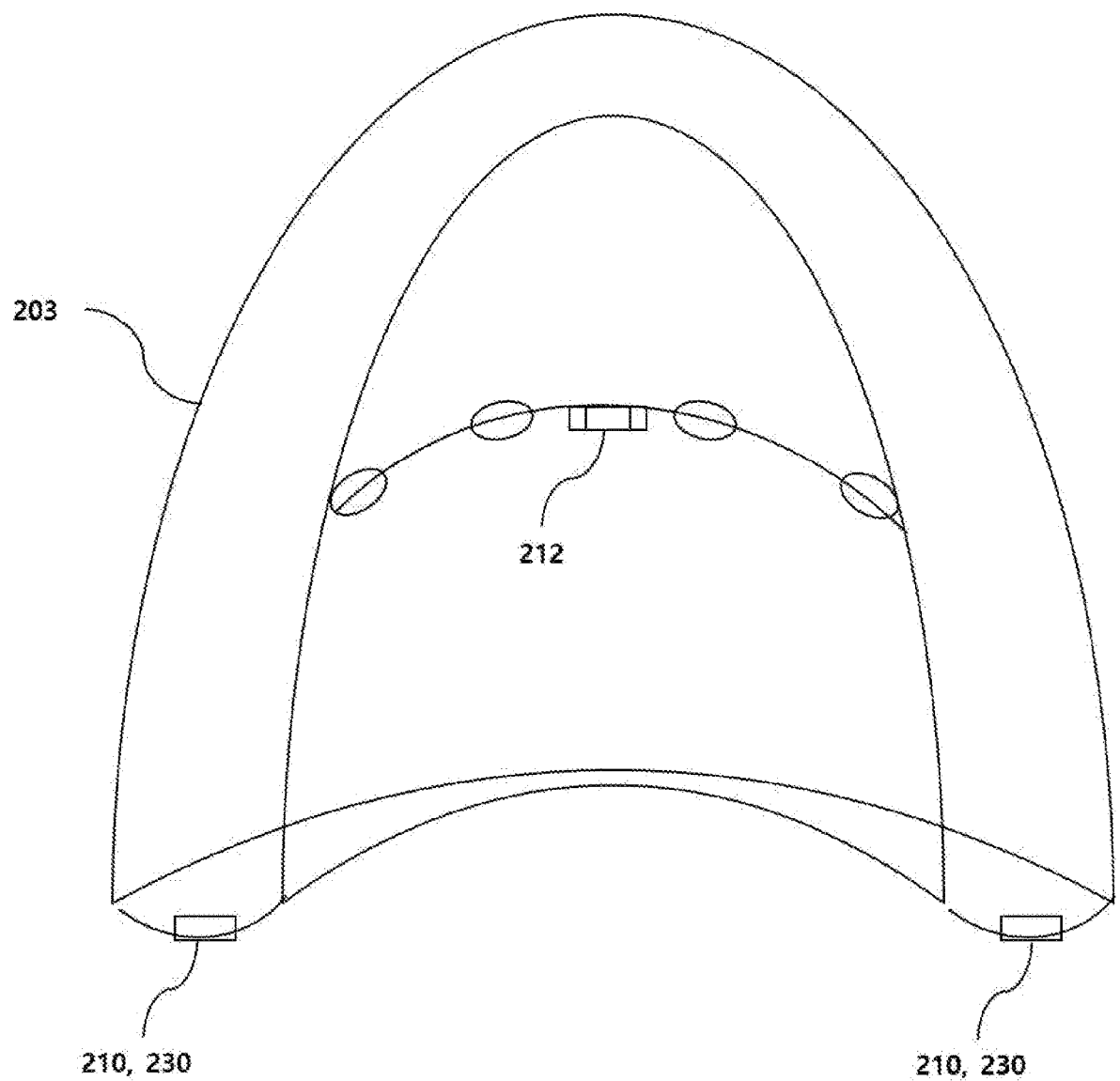
FIG. 7 shows the stimulation elements and the sensing elements located on the negative pressure cup according to the present invention, wherein the edge of the first diaphragm is enlarged.
Figure 22:
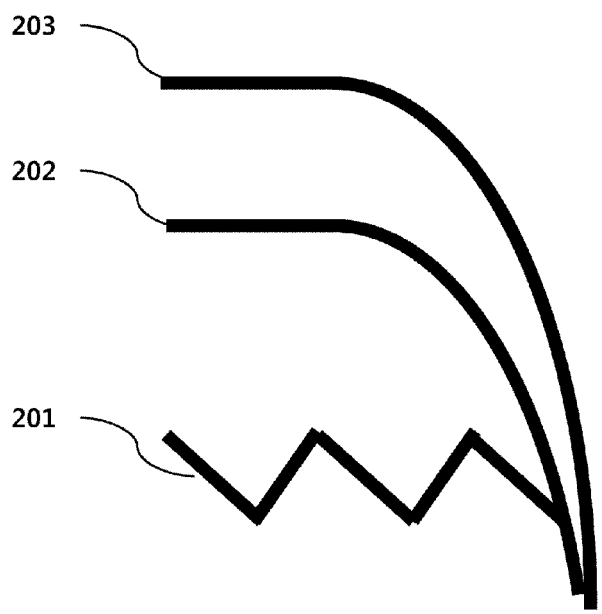
FIGS. 22 to 24 show a variety of surface shapes of the first diaphragm according to the present invention.
Figure 23:
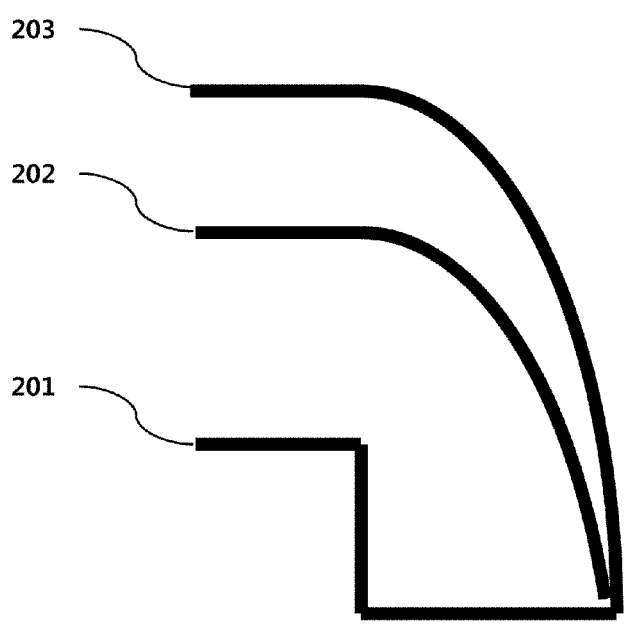
Figure 24:
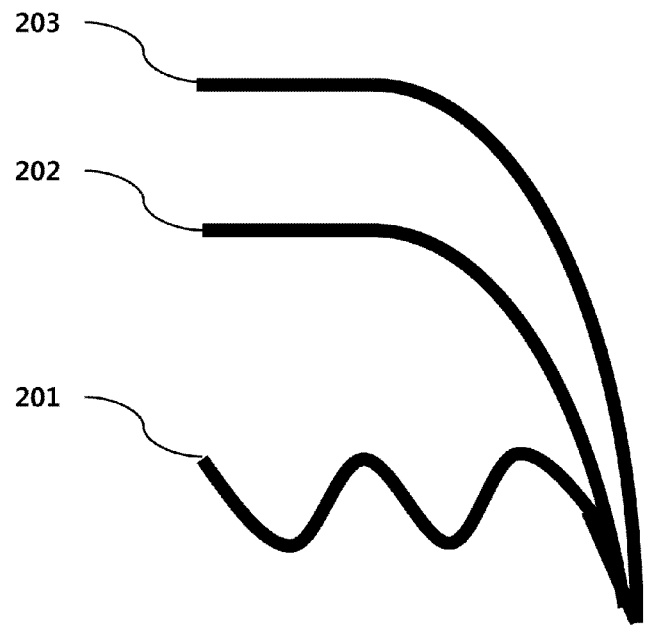

The first diaphragm 201 is semispherical or concave on the whole shape thereof, so that the skin is three-dimensionally deformed to the internal direction of the first diaphragm 201 when the negative pressure stimulation is applied and thus comes into close contact with the first diaphragm 201 and its concave and convex elements 207. Accordingly, as shown in FIG. 20b, the skin corresponds to the concave shape of the first diaphragm 201 and protrudes toward the concave side of the first diaphragm 201 when the negative pressure stimulation is applied. The first diaphragm 201 has a circular or polygonal sectional shape. At this time, the polygonal section is desirably square. As shown in FIGS. 22 to 24, the skin contact surface of the first diaphragm 201 desirably has a shape of a saw tooth, a cylinder or a wave, and additionally, it has various shapes of a plane, a pulse and others. Under the negative pressure stimulation, the three-dimensional deformation of the skin is variously controlled according to the shapes of the skin contact surface of the first diaphragm 201. As shown in FIG. 7, the edge region of the first diaphragm 201, which comes into contact with the skin, is expanded, and irrespective of the application of the negative pressure stimulation, the stimulation elements 210 and the sensing elements 230 are located on the edge region of the first diaphragm 201, so that separate stimulation is applied to the skin and the skin state is fed back. Accordingly, the edge region of the first diaphragm 201 is expanded to allow the stimulation elements 210 and the sensing elements 230 to be located thereon.

The first diaphragm 201 has the vents 204 formed thereon, and if necessary, it further has the concave and convex elements 207, the stimulation elements 210, and the sensing elements 230. Additionally, the first diaphragm 201 is heated by electricity to allow blood circulation to be improved, thus optimizing the composite stimulation effects of the negative pressure and the thermal stimulation.

In case of the multiple diaphragm structure according to the present invention, the second diaphragm 202 is located above the first diaphragm 201 and other diaphragms are sequentially located above or under the second diaphragm 202. The second diaphragm 202 is semispherical, concave, convex, or flat on a whole shape thereof and does not come into direct contact with the skin, unlike the first diaphragm 201. Further, the second diaphragm 202 is located above the first diaphragm 201 and flat on a whole shape thereof. As shown in FIG. 3, the second diaphragm 202 has the second vents 205 formed thereon, and if necessary, it serves as a support for the stimulation elements 210 and the sensing elements 230. In the same manner as the first diaphragm 201, the edge region of the second diaphragm 202 is expanded to allow the stimulation elements 210 and the sensing elements 230 to be located thereon. The first diaphragm 201 and the second diaphragm 202 are located along the path of the air flows (on the transmission paths of the negative pressure) in an upward direction from just above the skin (that is, toward the first diaphragm 201 from the skin).

According to the present invention, the housing 203 is a final diaphragm located at the outermost position of the negative pressure cup 200 and has the third vent 206 formed on the top or side surface thereof, thus finally discharging the air flowing in the upward direction from just above the skin. Through the first to third vents 204, 205, and 206 formed on the first diaphragm 201, the second diaphragm 202, and the housing 203, the negative pressure stimulation is applied over a large region of skin. The air ventilated through the third vent 206 of the housing 203 is accommodated by the body 400.

The surface of the first diaphragm 201 to be contacted with the skin is concave on the whole shape (for example, semispherical) so as to produce the negative pressure, provide efficient contact with the skin, and apply three-dimensional negative pressure stimulation to the skin. Further, the first diaphragm 201 has one or more concave and convex elements 207 located on the entire region or a partial region thereof, and the concave and convex elements 207 have one or more shapes selected from a cylinder, a sphere, a square pyramid, a triangular pyramid and so on, so that when the negative pressure stimulation is applied, the degree of the spatial rearrangements of the skin and subcutaneous tissues is controlled to the optimal shape and degree previously set according to the intended purpose of the effects in the skin. Further, the intensity of the negative pressure stimulation is continuously controlled by the controller 430 during the period of negative pressure stimulation, so that the temporal control of the three-dimensional stimulation of negative pressure can be effectively performed.

On the other hand, the variety of stimulation elements 210 and the sensing elements 230 are located on the first diaphragm 201, the second diaphragm 202, and the housing 203. In case of the triple diaphragm structure (See FIG. 3), for example, the third vents 206 are formed on the top or side surface of the housing 203 as the final diaphragm, thus discharging the air inside the negative pressure cup 200 to the outside. The respective diaphragms have the first to third vents 204, 205, and 206 adapted to transmit the negative pressure to the skin, and the air is finally discharged through the third vents 206 formed on the top or side surface of the housing 203 to the outside of the triple diaphragms. The respective diaphragms have semispherical, planar, or other shapes, and they have various sizes and formation positions. However, desirably, the first diaphragm 201 has a concave shape.

FIG. 1 shows the basic structure of the negative pressure cup 200 and FIG. 3 shows the triple diaphragm structure thereof. The basic structure of the negative pressure cup 200 has the first diaphragm 201 and the housing 203, and the triple diaphragm structure thereof has the first diaphragm 201, the second diaphragm 202, and the housing 203. The sizes, shapes and positions of the vents are differently formed. At this time, of course, the air inside the negative pressure cup 200 is finally discharged through the third vents 206 formed on the top or side surface of the housing 203 as the final diaphragm, thus allowing the negative pressure stimulation to be applied to the surface of the skin.

(First Diaphragm Separation Structure)

According to the present invention, the first diaphragm 201, which comes into direct contact with the skin, is coupled to the inside of the housing 203, as shown in FIG. 1, or is separated from the housing 203 as shown in FIG. 2. If the first diaphragm 201 is separated from the housing 203, that is, the first diaphragm 201 is coupled or connected to the housing 203 by means of first coupling elements 310 and second coupling elements 320. The first coupling elements 310 and the second coupling elements 320 are provided along the partial range of or the whole range of the circumference of the housing 203 and have a structure of selectively blocking and allowing the flow of air so as to effectively transmit the negative pressure. That is, the first diaphragm 201 is closed by the coupling elements to permit the flow of air to be formed only through the first vents 204 of the first diaphragm 201, so that the negative pressure stimulation is applied to the skin facing the first diaphragm 201. For example, the first coupling elements 310 and the second coupling elements 320 are formed of screws, screw grooves, and rubber packings. However, the first diaphragm 201 in the separable structure from the housing 203 has a module type, and accordingly, it is easily detachable from the housing 203. The structure of the first diaphragm 201 is made within the technological scope of the present invention. The formation of the separable first diaphragm 201 from the housing 203 gives a variety of advantages. Diverse types of the first diaphragm 201 may be used by attaching to the same housing 203, ensuring individualized and multi-purpose application of the negative pressure device. In addition, under the coupling structure of the first diaphragm 201, that is, the same negative pressure cup 200 is used for every patient, and accordingly, since the first diaphragm 201 comes into direct contact with the skin, sanitary problems happen. However, since the first diaphragm 201 has a module type under the separable structure from the housing 203, it is easily replaced after use, which is favorable from the sanitary point of view in that only the first diaphragm rather that the whole structure of the cupping cup can be easily replaced with a new one after it has offered direct contact with the skin. Furthermore, since the first diaphragm 201 has a module type under the separable structure from the housing 203, it is easily detachable from the housing 203, so that when the first diaphragm 201 is defective, only the first diaphragm 201 is exchanged with new one, which is more economical.

On the other hand, the first diaphragm 201 is separable from the negative pressure cup 200, and in the state where the separated first diaphragm 201 is first placed on the target area of the skin, after that, the negative pressure cup 200 is approached to and is connected to the first diaphragm 201 to apply the three-dimensional negative pressure stimulation to the skin. This form of application offers a practical and efficient procedure in such case as the target area of the skin and the type of the first diaphragm should be specifically selected. The most appropriate type of the first diaphragm 201 and the specific contact site of the skin can be efficiently selected by trying with a separated first diaphragm.

(Single Diaphragm Structure and Multiple Diaphragm Structure)

FIG. 1 shows a single diaphragm structure wherein the first diaphragm 201 and the housing 203 are provided, and FIG. 3 shows a multiple diaphragm structure wherein the first diaphragm 201, the second diaphragm 202, and the housing 203 are provided. According to the multiple diaphragm structure as shown in FIG. 3, the second diaphragm 202 is located above the first diaphragm 201 coming into direct contact with the skin, and the housing 203 as the final diaphragm is located above the second diaphragm 202. Each diaphragm is made of a hard or semi-hard material adapted to allow the concave and convex elements 207, the stimulation elements 210, and the sensing elements 230 to be located thereon, and further has the respective vents 204, 205 and 206 formed thereon, so that the negative pressure is transmitted through the vents finally to the relatively large area of the skin.

On the other hand, the first diaphragm 201 is made to a single semispherical shape, and otherwise, various module type first diaphragms are made and coupled or fixed to the inside of the housing 203. For example, a plurality of semispherical mesh frames are made and fixed or coupled to the inside of the housing 203, while having a given distance from each other with 203, thus forming the semispherical first diaphragm 201. At this time, the mesh holes become the first vents 204.

Under the single diaphragm structure or the multiple diaphragm structure, the whole concave shape of the first diaphragm 201 is adjusted to effectively limit the degree of deformation of the skin or subcutaneous tissues induced by the negative pressure stimulation, and further, the respective diaphragms are made of a hard or semi-hard material adapted to allow the stimulation elements 210 and the sensing elements 230 to be located thereon.

(Air Flows)

As shown in FIG. 4, the air flows producing the negative pressure are formed in an upward direction of the negative pressure cup 200 from just above of the skin. The respective air flows 101, 102 and 103 pass through the first to third vents 204, 205 and 206 of the first to third diaphragms 201, 202 and 203 and are then accommodated to the body 400. Accordingly, the air inside the negative pressure cup 200 is discharged to the body 400, and the air flows form the transmission paths of the negative pressure.

As shown in FIG. 4, the air flows 101, 102 and 103, along which the air inside the negative pressure cup 200 is discharged, are formed through the first vents 204 of the first diaphragm 201 to transmit the negative pressure stimulation to the skin, and the tissues of the skin are deformed in the inside direction of the negative pressure cup 200 and thus protrude toward the concave side of the first diaphragm 201. The first diaphragm 201 has one or more concave and convex elements 207 located on the entire region or a partial region thereof, and the concave and convex elements 207 have one or more shapes selected from a cylinder, a sphere, a square pyramid, a triangular pyramid and so on. Further, the first vents 204 are formed at the positions wherein the negative pressure is transmitted more intensively than other positions (for example, the skin contact surface of the first diaphragm 201, thus allowing the collagen fibers and elastin fibers of the skin and subcutaneous tissues facing the vents to be more intensively expanded and rearranged in the three-dimensional space through the negative pressure stimulation. Further, the intensity of the negative pressure stimulation is controlled through the controller 430 as time has passed, thus applying the three-dimensional negative pressure stimulation temporally. Through the spatially and temporally controlled stimulation of three-dimensional negative pressure optimal degree of stimulation for the purpose of the expected effect in the skin can be applied to the skin. When the stimulation of the negative pressure is applied, further, the maximum degree of deformation and protrusion of the skin and subcutaneous tissues is physically controlled within an appropriate limit by the semispherical or concave shape of the first diaphragm 201, thus effectively minimizing the risk of adverse reaction like excessive skin deformation due to the excessive stimulation of negative pressure stimulation or post-inflammatory hyperpigmentation related thereto. In the conventional suction or cupping cups, that is, if the individual's skin to which the negative pressure stimulation is applied and his or her physical characteristics are relatively weak or hypersensitive, or otherwise, if the negative pressure stimulation is excessive considering the individual characteristics of the subject, there are risk of excessive deformation of the skin and subcutaneous tissues and adverse reaction like venous bleeding. According to the present invention, however, the skin and subcutaneous tissues are deformed or protrude only to an appropriate degree offered by the semispherical or concave structure of the first diaphragm 201. Further, the sizes, shapes, and the degrees of concavity of the first diaphragm 201 are designed to offer a three-dimensional deformation of the skin tissues appropriate for such effects as anti-wrinkle, improved blood flow, whitening, moisturizing, and so on, and also, the intensity of the negative pressure stimulation is controlled by the controller 430, thus applying an optimized stimulation of negative pressure to the skin and subcutaneous tissues.

Further, light stimulation generated from the stimulation elements 210 located on the second diaphragm 202, for example, light stimulation LED elements 212 are irradiated to the skin underneath the first diaphragm 201 through the first vents 204 of the first diaphragm 201. In case of the conventional method of negative pressure stimulation combined with light stimulation, it is difficult to design an appropriate intensity of the light stimulation because there is considerable variation in the distance from the light emitting source to the surface of the deformed skin under negative pressure stimulation. The degree of deformation in the skin is hard to control. Accordingly, it is basically hard to optimize the composite stimulation of light applied together with the negative pressure stimulation, and further, there also exists a risk of adverse reactions due to poor control of the degree of skin deformation. According to the present invention, however, the points and their distances at which the light stimulation generated from the stimulation elements 210 located on the second diaphragm 202 arrive are infallibly calculated considering the degree of deformation of the skin offered by the first diaphragm 201, so that optimal intensity of the light stimulation are effectively calibrated. Further, electrical stimulation elements 211 are located on the first diaphragm 201 in such a manner as to come into direct contact with the skin to apply the stimulation to the skin.

(Vents and Concave and Convex Elements)

As shown in FIGS. 1 and 3, the first diaphragm 201 has the first vents 204 and the concave and convex elements 207, the second diaphragm 202 has the second vents 205, and the housing 203 has the third vents 206. The first vents 204 and the second vents 205 are ventilation holes (or air holes), through which the negative pressure stimulation is transmitted to the skin. Particularly, the intensity of the negative pressure stimulation is higher in the skin region facing the vents than other skin regions.

While serving as the ventilation holes through which the air passes, on the other hand, the first to third vents 204 to 206 serve as paths for such stimulations as generated from the stimulation elements 210 disposed on the second diaphragm 202 and the housing 203 to approach to the skin, and serve as paths or windows of the sensing elements 230 disposed on the second diaphragm 202 and the housing 203 to monitor the state of the skin. Accordingly, the negative pressure cup 200 according to the present invention is provided with the stimulation elements 210 and the sensing elements 230, thus conducting such functions as composite stimulation and composite monitoring performed simultaneously. The first vents 204 and the second vents 205 are formed along the concave semispherical surfaces of the first diaphragm 201 and the second diaphragm 202, and the third vents 206 are formed on the top or side surface of the housing 203. The first to third vents 204 to 206 have shapes of fine dot-like holes, so that the corresponding diaphragms look like nets, and in addition, they may show various shapes such as a line, a circle, a polygon, a character, a symbol, and a plate. The third vents 206, through which the air inside of the negative pressure cup 200 is finally discharged, are formed on the top or side surface of the housing 203. The first to third vents 204 to 206 generally serve as the ventilation holes through which the air passes, and they may have various shapes. According to the present invention, therefore, the shapes of the first to third vents 204 to 206 are not limited specifically.

As shown in FIGS. 1 and 3, the first diaphragm 201 has the concave and convex elements 207. Through the formation of the concave and convex elements 207, the partial deformation of the skin is adjusted to the optimal degree of deformation designed previously, upon the application of the negative pressure stimulation to the skin. Accordingly, the deformation of the skin can be three-dimensionally shaped with diverse positions and shapes of the concave and convex elements 207. So as to adjust the structural deformation of the skin and subcutaneous tissues three-dimensionally, one or more concave and convex elements 207 are located on the entire region or a partial region thereof (See FIGS. 8 to 11), and the concave and convex elements 207 have one or more shapes selected from a cylinder, a sphere, a square pyramid, a triangular pyramid and so on.

Under the negative pressure stimulation through the conventional suction cup or cupping cup, it is difficult to limit the degree of deformation of the skin and subcutaneous tissues caused by the negative pressure stimulation within an appropriate range. According to the present invention, however, the deformation of the skin and subcutaneous tissues is limited to an appropriate degree according to the degree of concavity in the whole shape of the first diaphragm 201, thus effectively minimizing any risk of adverse reactions like post-inflammatory hyperpigmentation. Through the three-dimensional deformation induced by the concave and convex elements 207, the first vents 204 of various sizes, shapes, formation positions, and numbers, and the concave surface of the first diaphragm 201, furthermore, the components of the skin and subcutaneous tissues such as keratin, melanocyte, collagen, elastin fibers, blood vessels, lymph, nerves, Meissner's corpuscle, Pacinian corpuscle and so on are variously deformed in three-dimensional forms, thus applying efficient stimulation for the improvement of the functions of the skin. In addition, the intensity of negative pressure is continuously controlled through the controller 430 during the negative pressure stimulation, which control is effectively modulated with reference to the information on the current state of the individual's skin monitored by the sensing elements 230, so that customized and individualized stimulation of three-dimensional negative pressure offers an optimal stimulation for the improvement of the skin functions.

(Stimulation Elements and Sensing Elements)

The sensing elements 230 include a temperature sensor 231, an impedance sensor 232, a blood flow sensor 233, and a pressure sensor 234, and they are mounted on the diaphragms of the negative pressure cup 200 or formed integrally therewith. If they are mounted thereon, they are located on specific regions of the diaphragms. If they are formed integrally therewith, the circuits for driving the sensing elements 230 are also formed integrally with the diaphragms.

The impedance sensor 232 is adapted to measure impedance in the skin contact area with the cupping device and has an amplifier if needed. The temperature sensor 231 is used individually or together from or with a non-contact infrared sensor or a contact sensor and serves to measure the temperature of the skin surface or the surrounding temperature. At this time, an element like an ultra-small thermistor or an ultra-precision thermocouple is used to measure the temperature of the skin. The blood flow sensor 233 includes an LED light source and a photodiode and serves to convert the optical data reflecting the amount of blood flowing along the blood vessel in the target area of the skin into a current or voltage signal. The LED light source is used also for the light stimulation. The pressure sensor 234 serves to measure the pressure of the negative pressure cup 200 so as to feed back the state of the negative pressure.

The stimulation sensors 210 include the electrical stimulation elements 211, the light stimulation LED elements 212, and the thermal stimulation elements. The electrical stimulation elements 211 are formed of electrode plates with different potentials. A plurality of electrode plates may be located so as to allow micro current to be uniformly applied. The LED light sources of the light stimulation LED elements 212 are used with the LEDs having wavelength bands effective in the skin stimulation, and at this time, one or more wavelength bands are provided in a single or plural combination thereof. Light emitting elements are provided as the thermal stimulation elements.

On the other hand, the light stimulation LED elements 212 are used for the light stimulation. As another element for the light stimulation, laser elements have very limited irradiation points when compared with the LED elements 212, so that it is hard to conduct the composite stimulation over the whole internal region of the skin contact surface of the negative pressure cup 200. Accordingly, the light stimulation is usually applied through the LED elements, but the laser elements may be used if needed.

(Arrangements of Vents, Concave and Convex Elements, Stimulation Elements and Sensing Elements)

Figure 5:
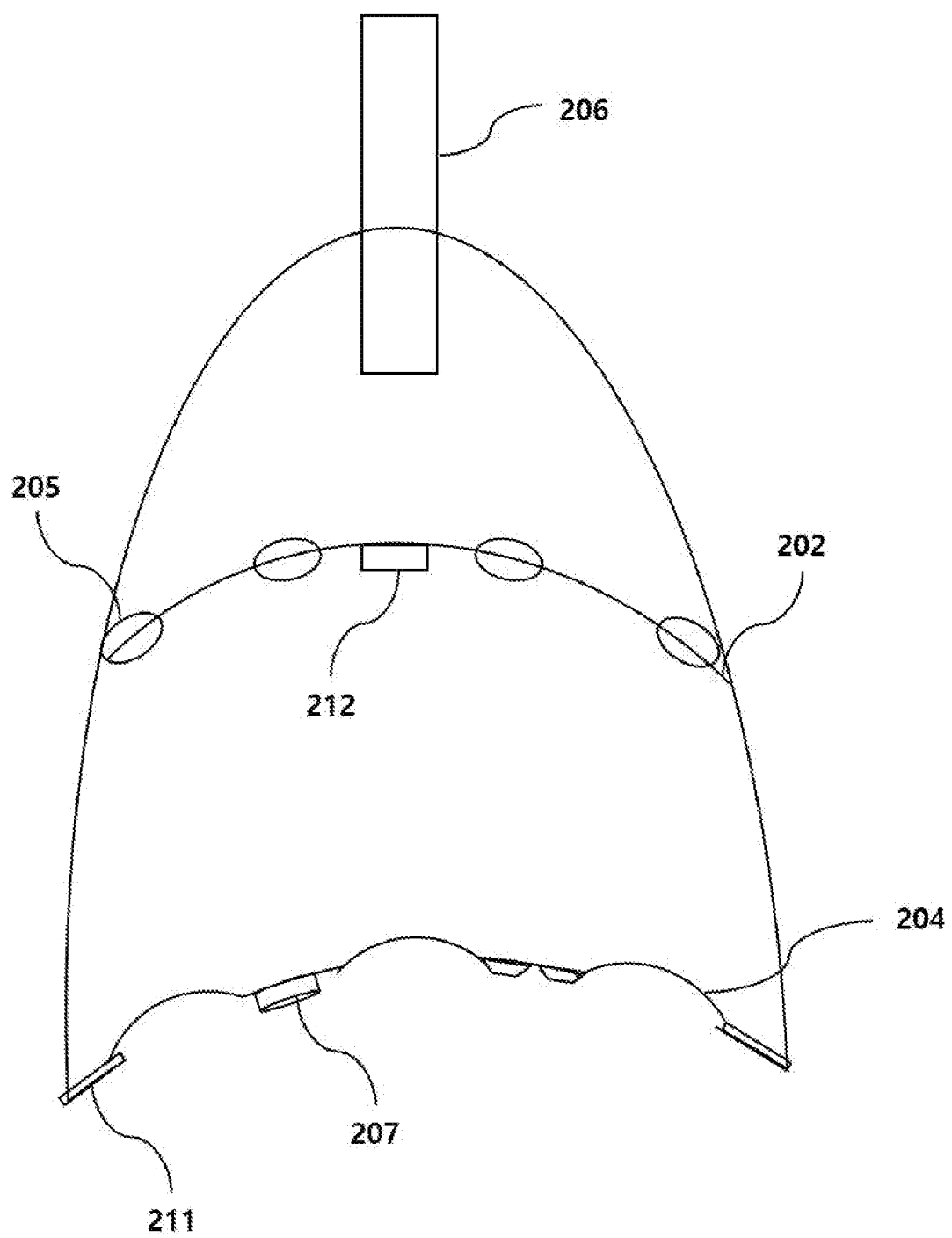
FIGS. 5 and 6 show stimulation elements and sensing elements located on the diaphragm of the negative pressure cup according to the present invention.

FIG. 5 shows the stimulation elements 210 of the first diaphragm 201 and the second diaphragm 202. The stimulation elements 210 have various kinds, sizes, shapes, formation positions and numbers thereof, and as shown in FIG. 5, the electrical stimulation elements 211 are located on the first diaphragm 201, while the light stimulation elements 212 are being located on the second diaphragm 202. According to the conventional negative pressure and composite stimulation device, disadvantageously, it is very limited in locating the stimulation elements within the cupping cup, and otherwise, when other stimulation is applied, the negative pressure stimulation is considerably limited. According to the present invention, however, the first diaphragm 201, the second diaphragm 202, and the housing 203 serve as rigid supports for stimulation elements or sensing elements, so that the stimulation elements 210 can be located on the diaphragms, while having various kinds, sizes, shapes, formation positions and numbers thereof.

When the negative pressure stimulation is applied to the skin via the first diaphragm 201, the skin is deformed and protrudes to come into close contact with the first diaphragm 201. At this time, the micro current stimulation through the electrical stimulation elements 211 of the first diaphragm 201 and the light stimulation generated from the light stimulation LED elements 221 of the second diaphragm 202 are applied to the skin through the first vents 204 of the first diaphragm 201, thus allowing the skin to be stimulated. In case of the conventional negative pressure stimulators that also provides a composite stimulation of electrical currents or light, upon the application of the negative pressure stimulation, the area to which the electrical stimulation is applied are so limited that the electrical stimulation is applied just to the circular rim of the contact area facing the negative pressure cup, or the points to which the light stimulation is applied are very limited, so that the points to which the electrical stimulation or the light stimulation are applied disadvantageously do not correspond to the relatively large region to which the negative pressure stimulation is applied. According to the present invention, however, the first vents 204 with various sizes, shapes, formation positions and numbers are formed on the first diaphragm 201, and accordingly, the electrical stimulation and the light stimulation are applied over the whole region of the skin contact surface as well as the circular rim of the contact area facing the concave negative pressure cup 200, so that the negative pressure stimulation, the electrical stimulation, and the light stimulation are applied over almost the same region as the first diaphragm 201. That is, advantageously, the composite stimulation is applied stably to the whole region facing the first diaphragm 201. Further, the skin state is monitored by the sensing elements 230, and accordingly, various stimulation is adjusted and applied reflecting the current state of the skin of the individual, thus achieving a customized stimulation over the whole region of the skin.

Figure 6:
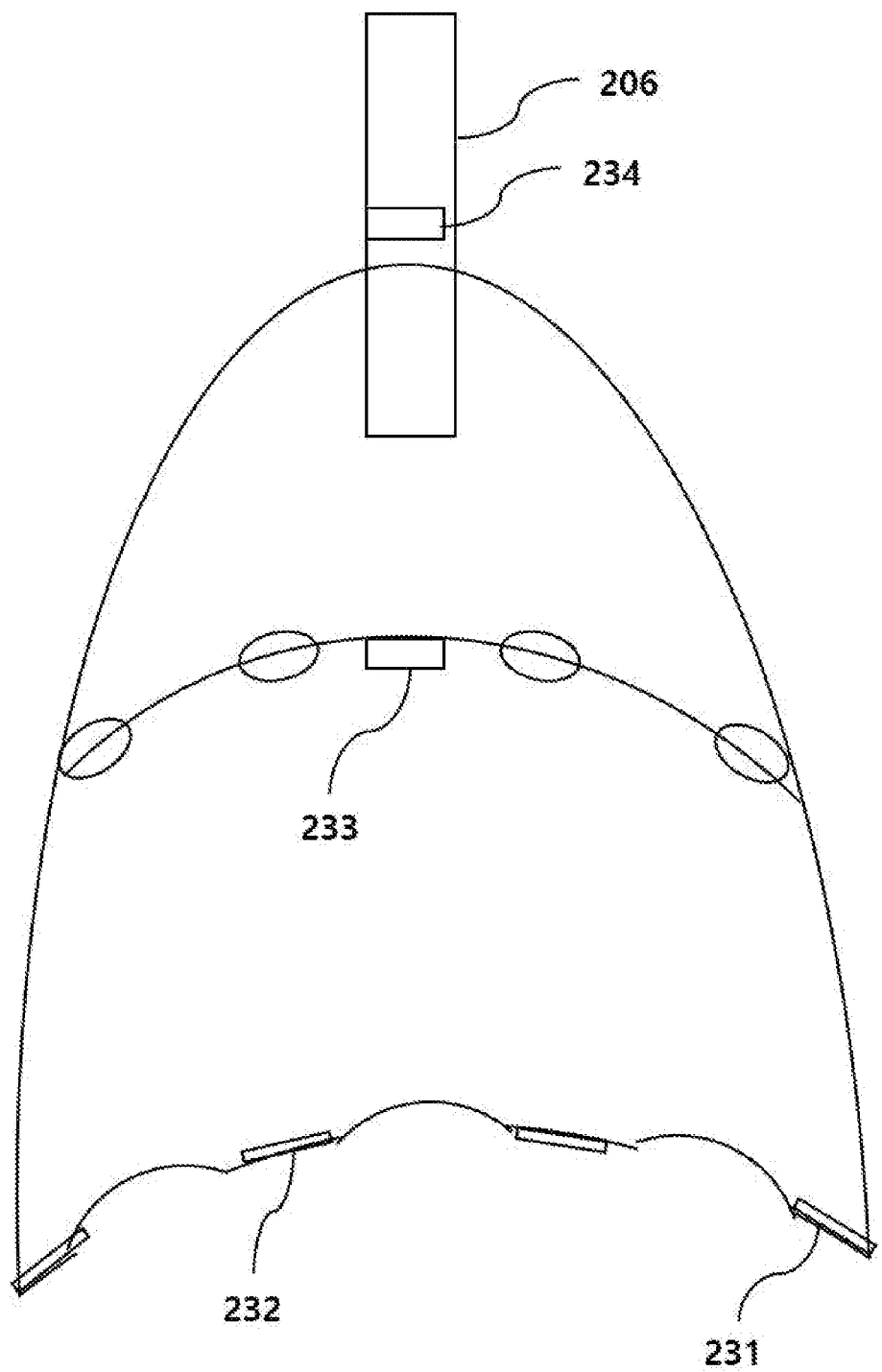

FIG. 6 shows the sensing elements 230 located on the respective diaphragms. The sensing elements 230 are varied in kinds, sizes, shapes, formation positions and numbers thereof. In case of the conventional negative pressure and composite stimulation device, disadvantageously, it is very limited in locating the sensing elements within the cupping cup, and otherwise, the sensing elements are located, while the negative pressure stimulation is being limited. According to the present invention, however, the first diaphragm 201, the second diaphragm 202 and the housing 203 serve as rigid supports for the sensing elements and the vents of the respective diaphragms serve to gently transmit the negative pressure through the respective diaphragms, so that the sensing elements can be located on the respective diaphragms to monitor the current state of the skin through the vents as windows to the skin, without having any limitation in the application of the negative pressure stimulation. The risk that the efficiency of the negative pressure stimulation is decreased or the negative pressure stimulation is distorted is minimalized by adopting such strategy that the sensing elements are firmly located onto the diaphragm and the sensing elements directly face the skin through the vents. As shown in FIG. 6, the temperature sensor 231 and the impedance sensor 232 are located on the first diaphragm 201, the blood flow sensor 233 on the second diaphragm 202, and the pressure sensor 234 on the housing 203. If necessary, however, the arrangements of the stimulation elements 210 and the sensing elements 230 as shown in FIGS. 5 and 6 may be freely changed.

Figure 8:
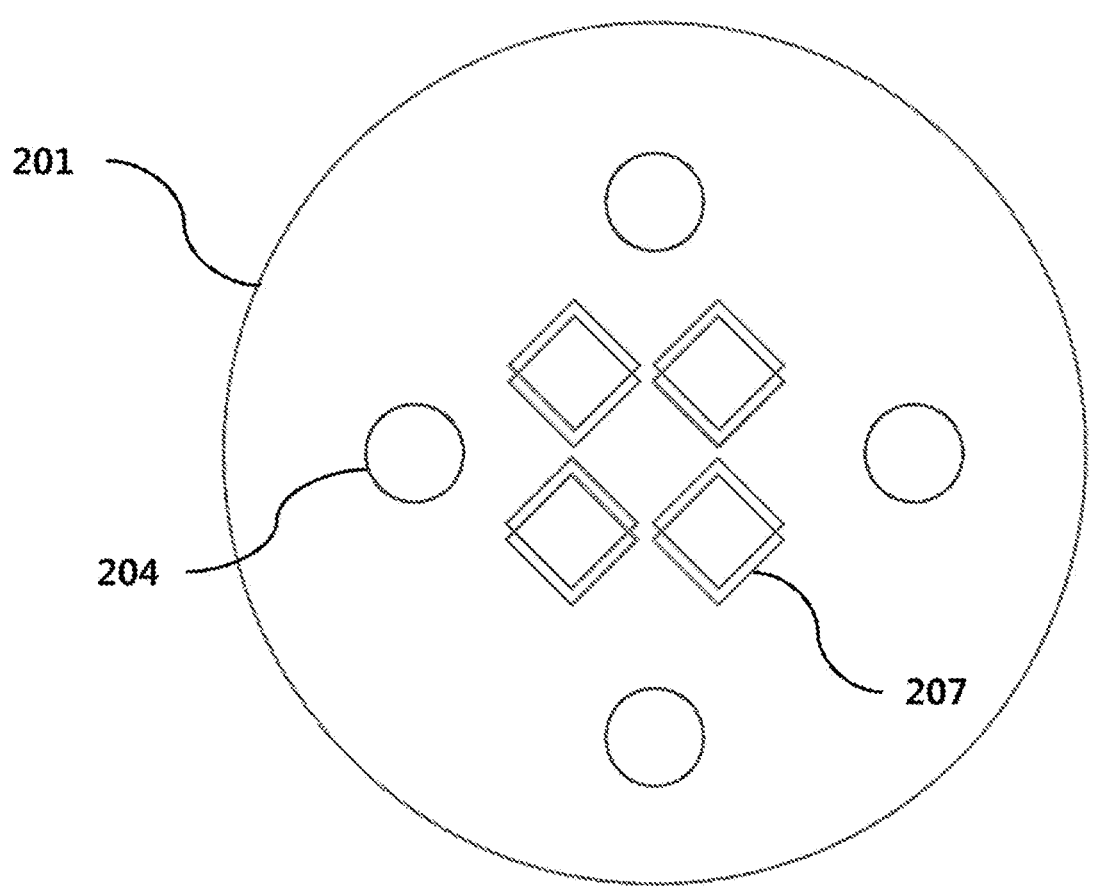
FIGS. 8 and 9 show the first diaphragm having a circular shape when viewed from the below thereof, wherein vents and concave and convex elements have various shapes, sizes, and numbers.
Figure 9:
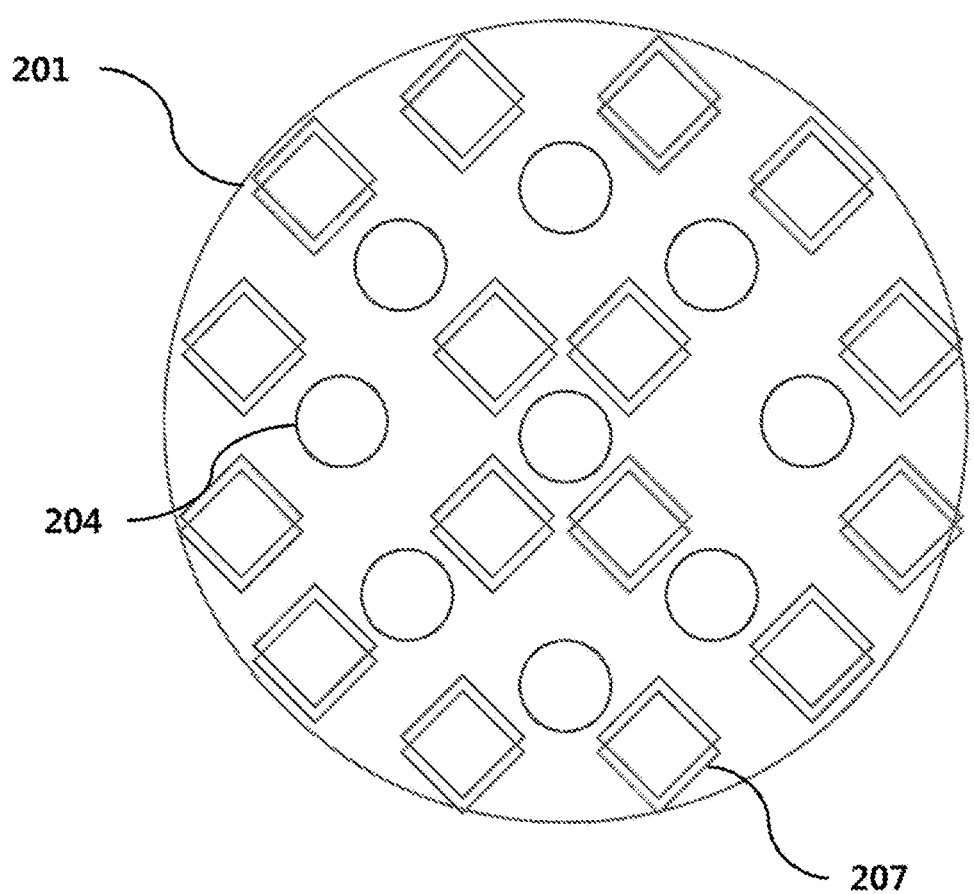
Figure 10:
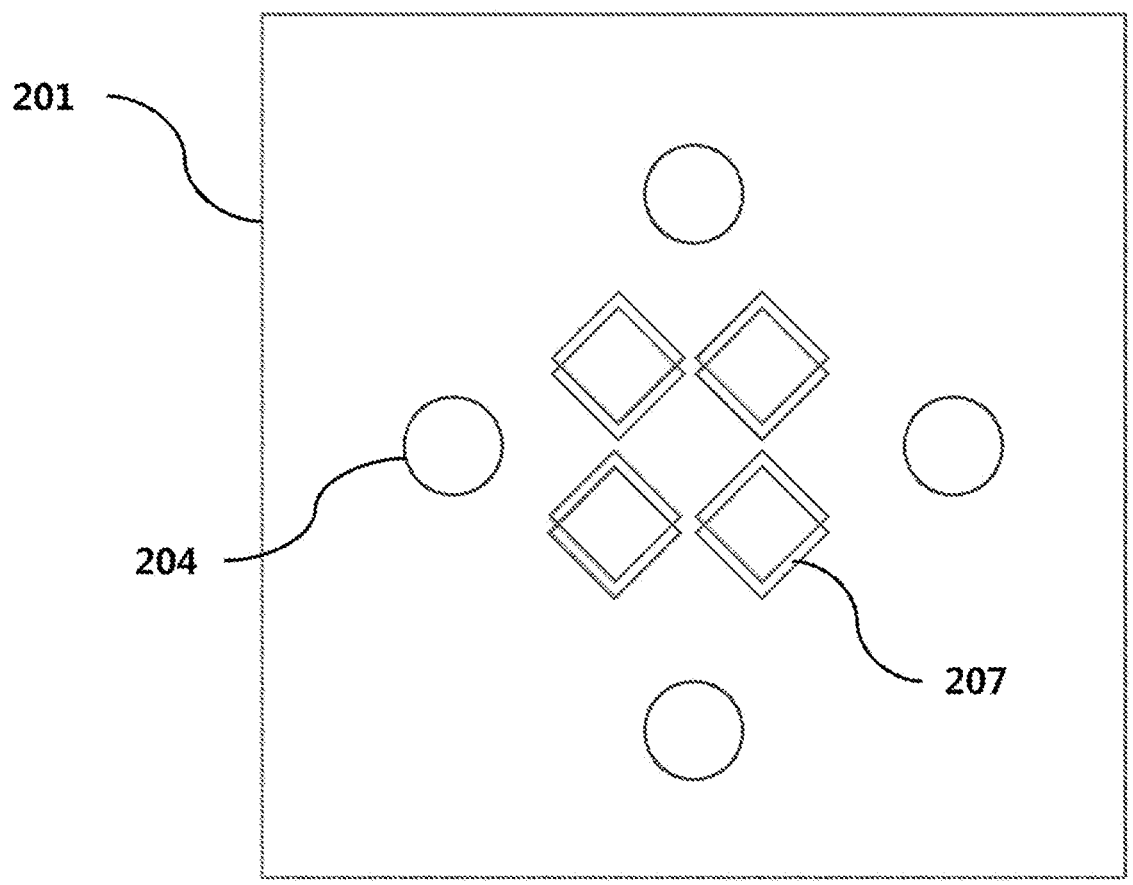
FIGS. 10 and 11 show the first diaphragm having a square shape when viewed from the below thereof, wherein vents and concave and convex elements have various shapes, sizes, and numbers.
Figure 11:
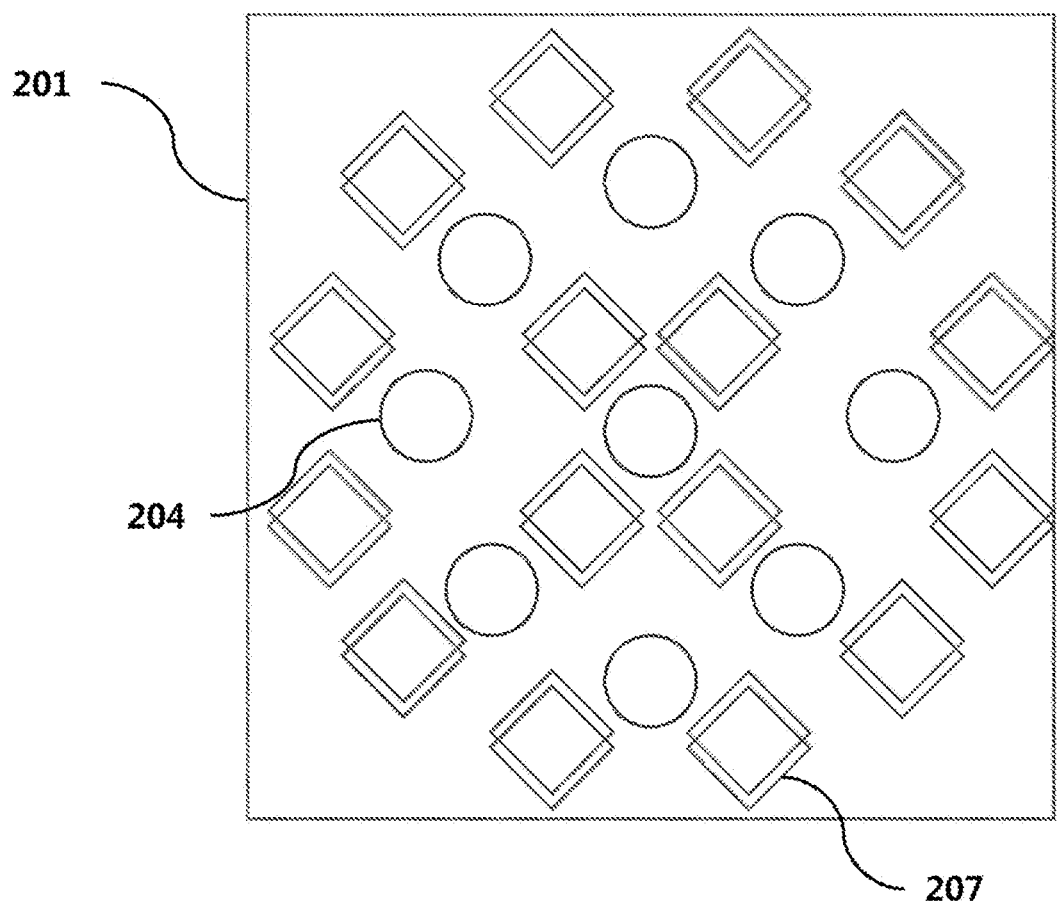

The first vents 204 of the first diaphragm 201 pair up or mix with the concave and convex elements 207, as shown in FIGS. 8 and 9. FIG. 8 shows the first vents 204 and the concave and convex elements 207 formed on a portion of the region of the first diaphragm 201, and FIG. 9 shows the first vents 204 and the concave and convex elements 207 formed on the whole region of the first diaphragm 201. The first diaphragm 201 as shown in FIGS. 8 and 9 has a circular sectional shape, and that as shown in FIGS. 10 and 11 has a square sectional shape. The formation positions of the first vents 204 and the concave and convex elements 207 as shown in FIGS. 10 and 11 are the same as those in FIGS. 8 and 9, and the sectional shape of the first diaphragm 201 as shown in FIGS. 10 and 11 is not different from that as shown in FIGS. 8 and 9. As shown in FIGS. 8 to 11, the first vents 204 and the concave and convex elements 207 can have various sizes, shapes, formation positions and numbers thereof.

Figure 12:
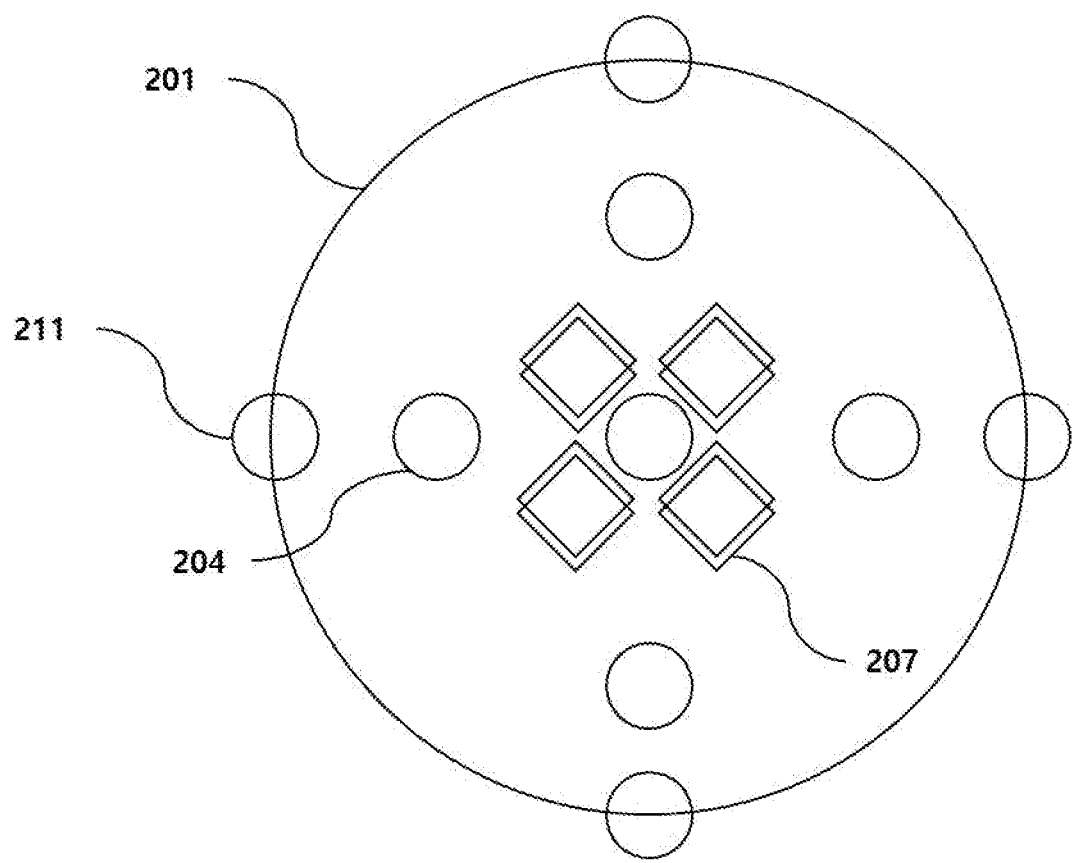
FIGS. 12 and 13 show the first diaphragm viewed from the below thereof, wherein electrical stimulation elements, vents and concave and convex elements have various shapes, sizes, and numbers.
Figure 13:
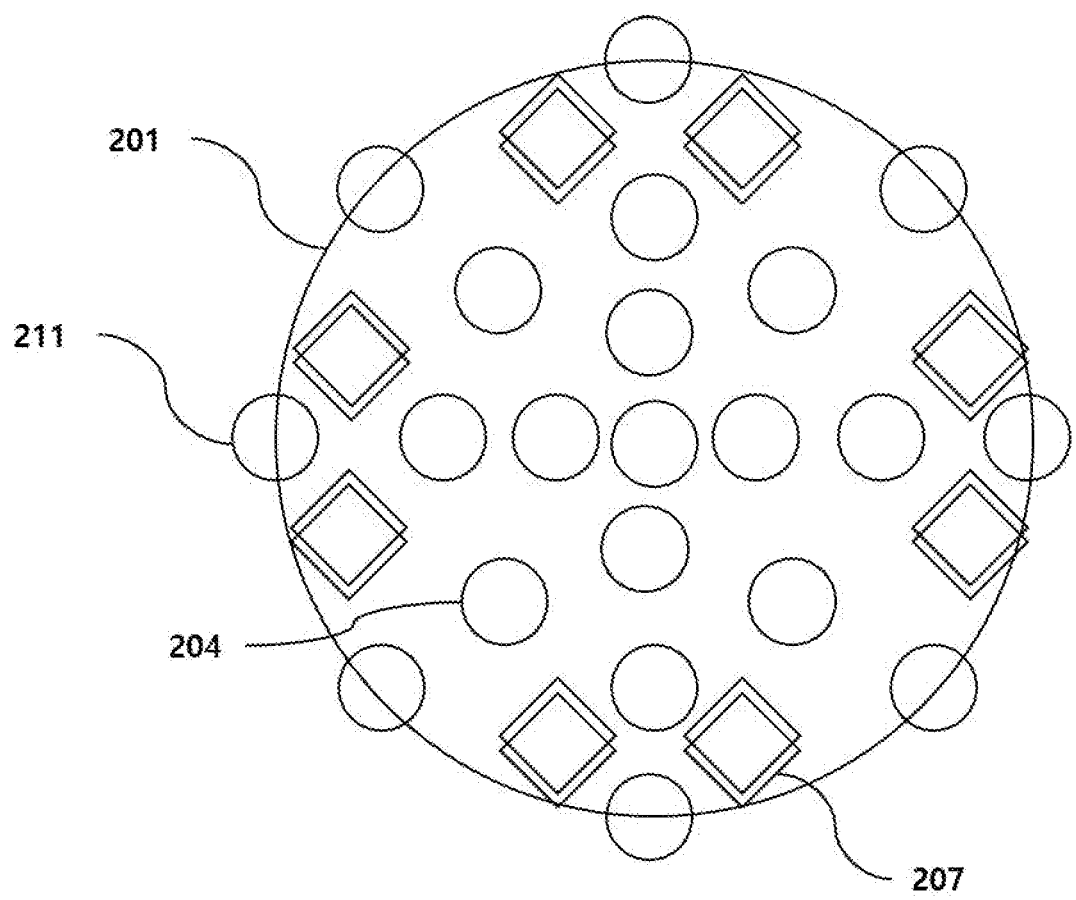

FIGS. 12 and 13 show various arrangements of the stimulation elements 210 on the first diaphragm 201. The stimulation elements 210 having various sizes, shapes, formation positions and numbers thereof are located, while avoiding the positions on which the first vents 204 are formed.

Figure 14:
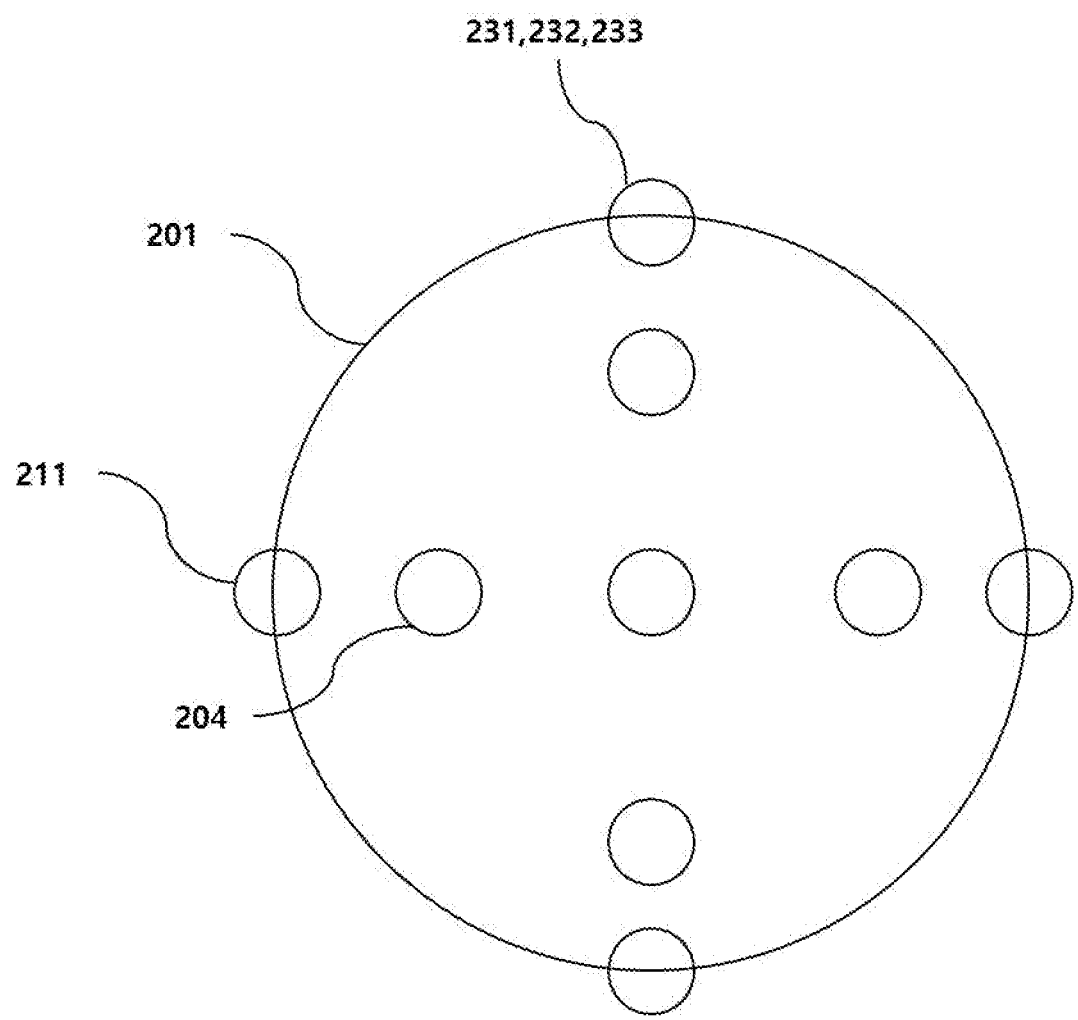
FIGS. 14 and 15 show the first diaphragm viewed from the below thereof, wherein stimulation elements, sensing elements, vents and concave and convex elements have various shapes, sizes, and numbers.
Figure 15:
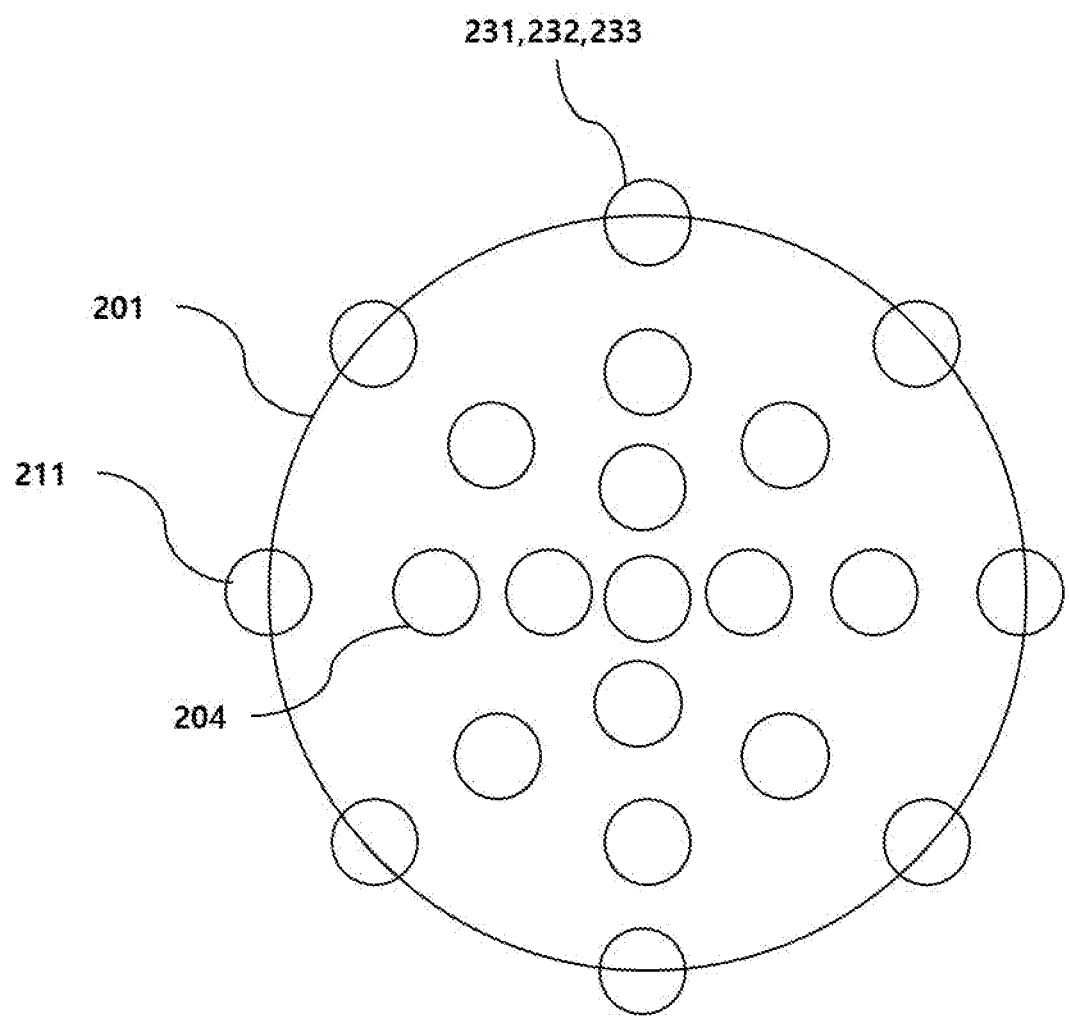

FIGS. 14 and 15 show various arrangements of the stimulation elements 210 and the sensing elements 230 on the first diaphragm 201. The electrical stimulation elements 211, the temperature sensor 231, the impedance sensor 232, and the blood current sensor 233 having various sizes, shapes, formation positions and numbers thereof are located on the first diaphragm 201, while avoiding the positions on which the first vents 204 are formed.

Figure 16:
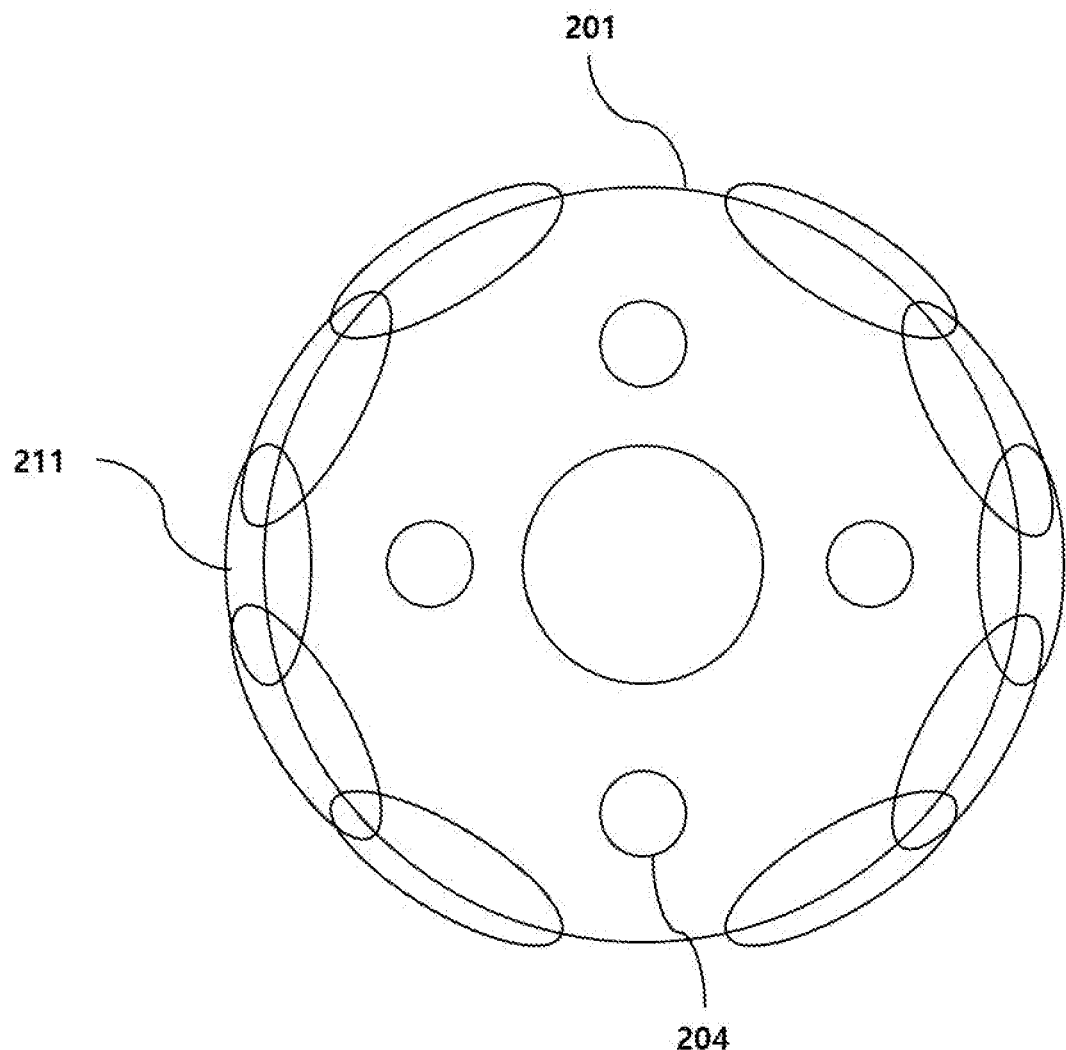
FIGS. 16 and 17 show the first diaphragm viewed from the below thereof, wherein stimulation elements have various sizes and formation positions.
Figure 17:
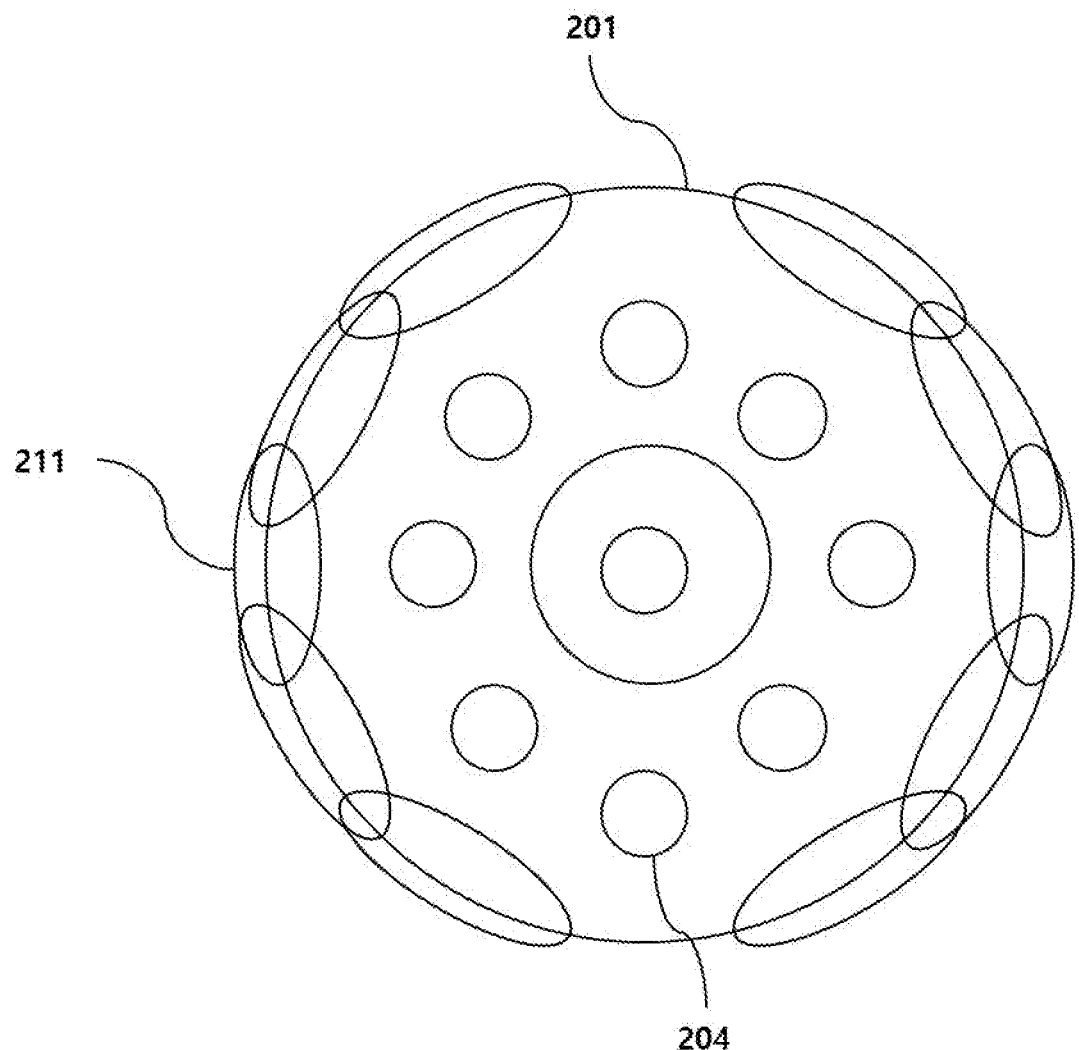
Figure 18:
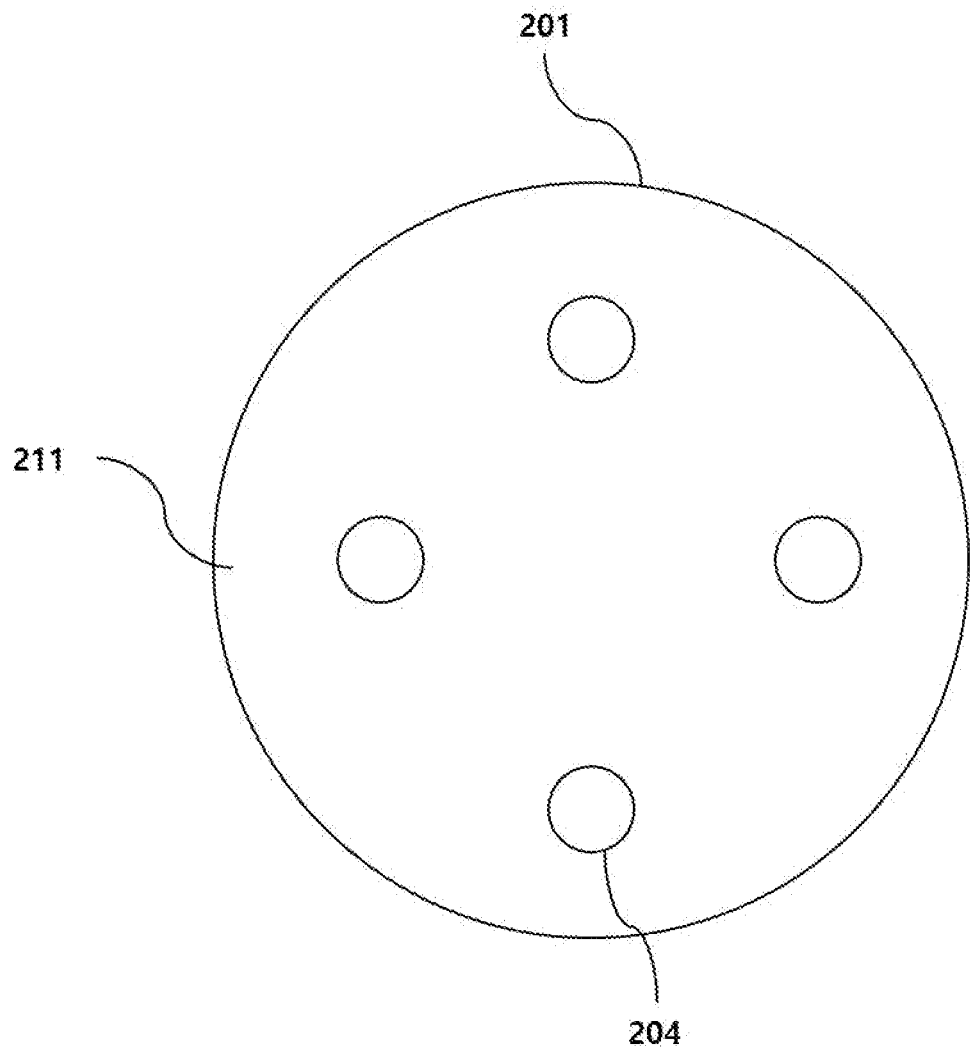
FIGS. 18 and 19 show the first diaphragm viewed from the below thereof, wherein the size and shape of the stimulation element are the same as those of the first diaphragm.
Figure 19:
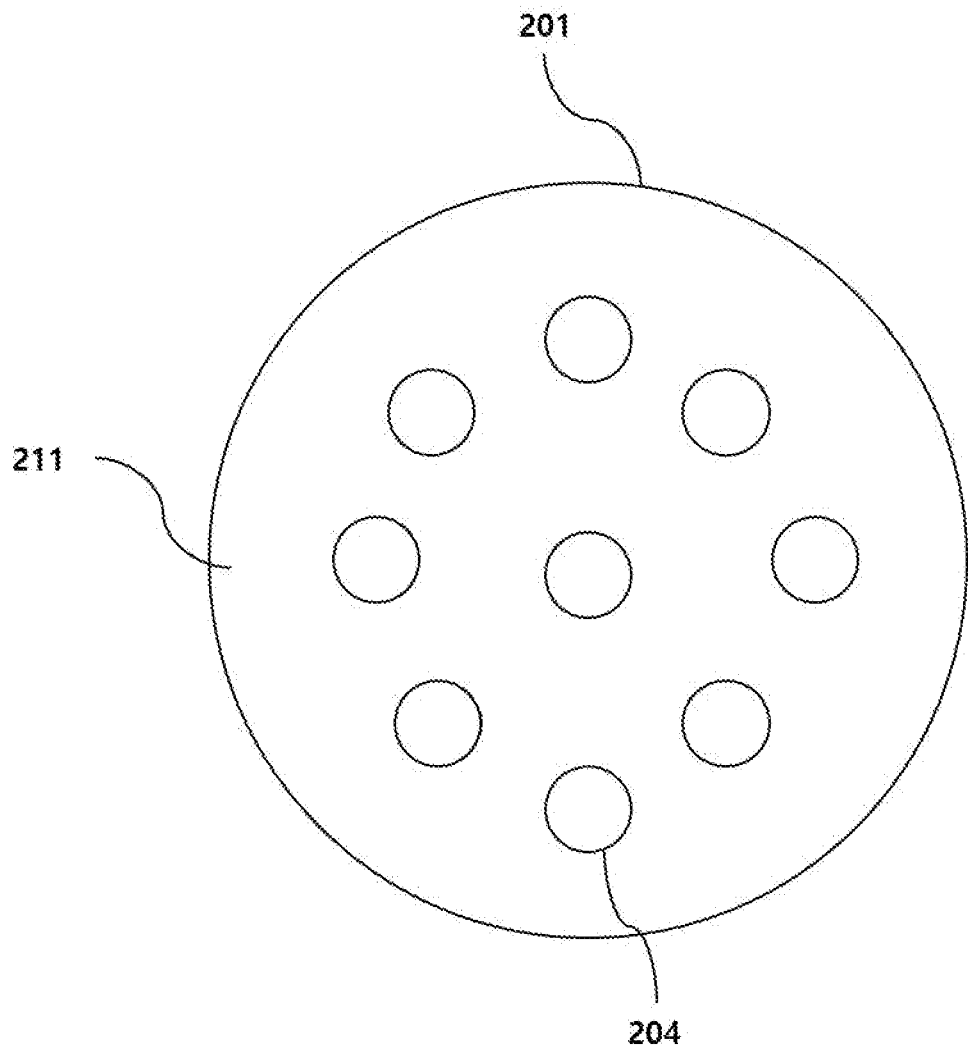

FIGS. 16 and 19 show various sizes and positions of the stimulation elements 210 on the first diaphragm 201. The electrical stimulation elements 211 having various sizes, shapes, formation positions and numbers thereof are located on the first diaphragm 201, while avoiding the positions on which the first vents 204 are formed. FIGS. 18 and 19 show the electrical stimulation elements 211 having the same sizes and shapes as the first diaphragm 201. That is, the whole region of the first diaphragm 201 except for the first vents 204 serves as the electrical stimulation elements 211.

(Distance Adjustment of First Diaphragm)

Figure 25:
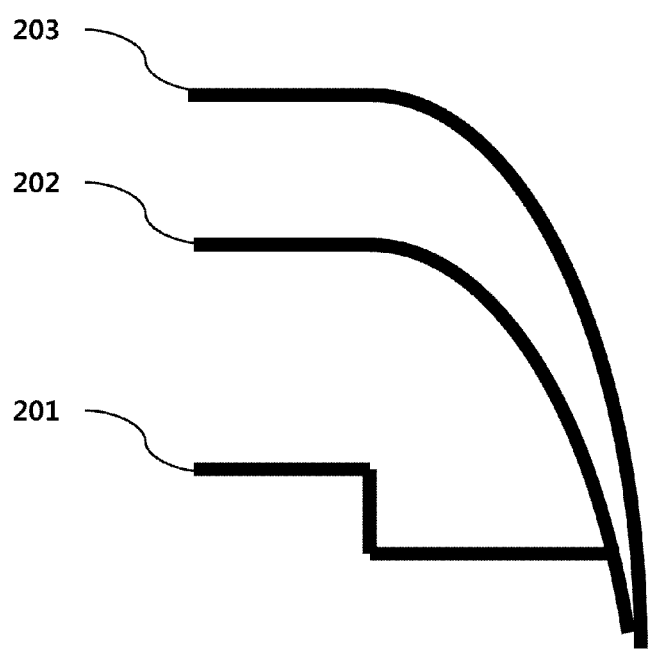
FIGS. 25 and 26 show the first diaphragm adjusted in height, wherein the first diagram is located by a long distance from the skin surface, and otherwise, the negative pressure stimulation is applied collectively to a small target region.
Figure 26:
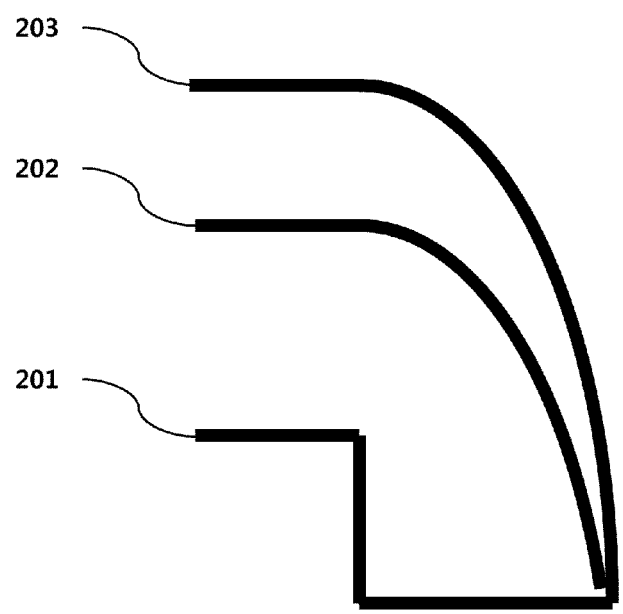

FIGS. 25 and 26 show various positions of the first diaphragm 201. As mentioned above, the first diaphragm 201 is separable from the housing 203, and after the first diaphragm 201 is brought into contact with the target skin region, in this case, the negative pressure stimulator or the cupping cup or suction cup for negative pressure stimulation comes into contact with the top of the first diaphragm 201 or the periphery thereof, so that upon the application of the negative pressure stimulation, the negative pressure stimulation can be applied three-dimensionally to the skin with the help of the first diaphragm 201. Further, as shown in FIG. 25, the first diaphragm 201 is located by a relatively long distance from the skin surface, so that a given distance from the whole region of the target skin is maintained to accommodate deformation of the skin, and as shown in FIG. 26, only a given region of the first diaphragm 201 is located by a relatively long distance from the skin surface, so that the negative pressure stimulation can be applied collectively to a relatively small region of the target skin. According to the desired purposes, therefore, the distance between the first diaphragm 201 and the target skin is increased appropriately, and otherwise, the negative pressure stimulation is applied collectively to the relatively small region of the target skin.

(Body)

Figure 27:
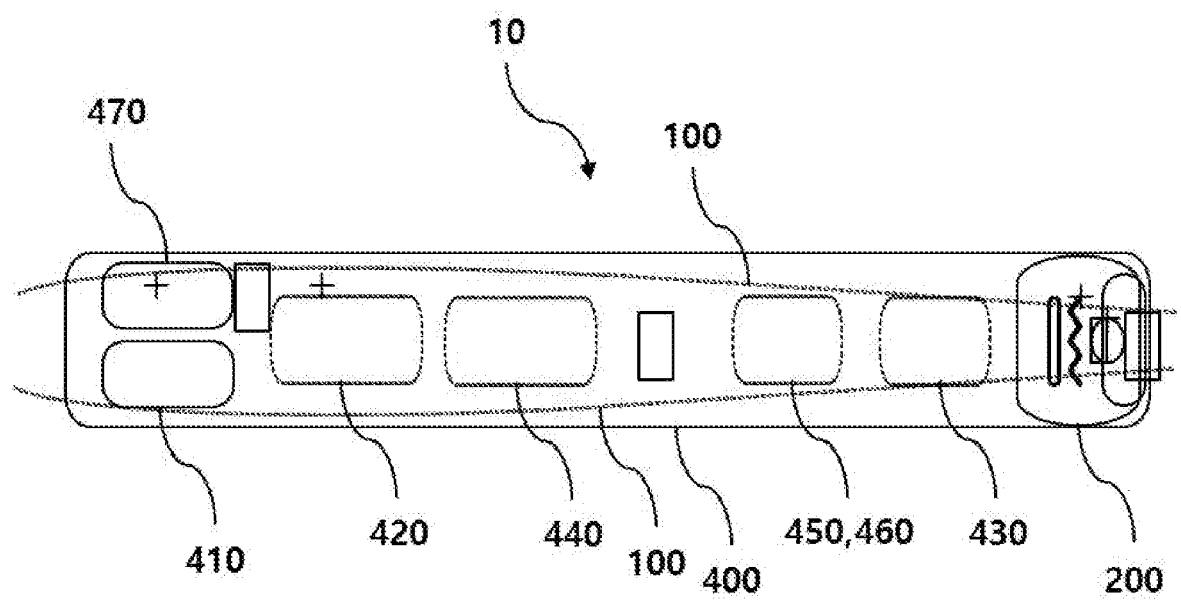
FIG. 27 shows a configuration of a three-dimensional negative pressure stimulator according to the present invention.

As shown in FIG. 27, the three-dimensional negative pressure stimulator 10 according to the present invention is configured wherein the body 400 having a USB charger 410, a manipulator 420, the controller 430, a battery 440, a motor 450, a fan 460 and a PCB 470 is coupled or connected to the negative pressure cup 200, thus applying the three-dimensional negative pressure stimulation to the skin. The USB charger 410 is a USB terminal for charging the portable three-dimensional negative pressure stimulator 10, and the battery 440, which supplies electricity to the three-dimensional negative pressure stimulator 10, is a lithium-ion battery. According to the present invention, of course, the charger and the battery may have various charging methods and battery kinds, while being limited thereto. Therefore, various charging methods and battery kinds are selected according to the use of the portable three-dimensional negative pressure stimulator 10 or the fixed type three-dimensional negative pressure stimulator 10. At this time, the fixed type three-dimensional negative pressure stimulator 10 is the stimulator used with normal power. The USB charger 410 and the battery 440 as a power supply part receive the power from an external power terminal and supply the power necessary for the operation of the three-dimensional negative pressure stimulator 10.

Figure 28:
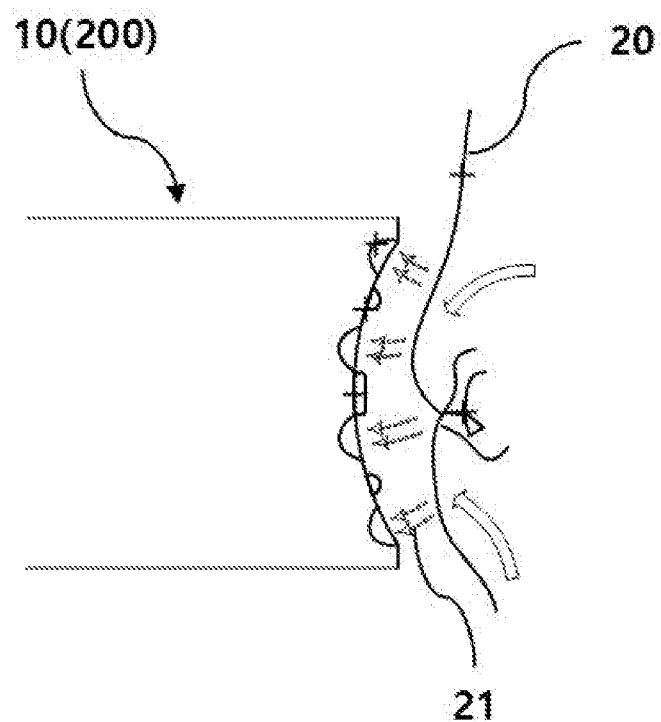
FIG. 28 shows the negative pressure stimulation generated from skin.

The motor 450 and the fan 460 operate by control signals of the controller 430 to induce the air flows 100 as shown in FIG. 27, thus allowing the negative pressure to be generated. That is, if the motor 450 and the fan 460 operate, the air flows 100 are induced toward the diaphragms of the negative pressure cup 200 from just above the skin to allow the air to pass through the vents, and next, the air flows 100 are induced toward the body 400 from the negative pressure cup 200 to allow the negative pressure to be generated. If the negative pressure is generated, as shown in FIG. 28, the skin 20 protrudes toward its protruding directions 21 (or toward the negative pressure cup 200), so that it is under the negative pressure stimulation. The intensity of the negative pressure is varied in accordance with the driving speeds of the motor 450 and the fan 460 controlled by the controller 430.

The PCB 470 has a variety of elements and circuits disposed thereon so as to drive the USB charger 410, the manipulator 420, the battery 440, the motor 450, and the fan 460. The manipulator 420 has a variety of buttons mounted thereon, so that the three-dimensional negative pressure stimulator 10 is manipulated by the user, and otherwise, the manipulator 420 includes a touch screen for the manipulation. In addition, a display (not shown) may be provided to in real time display the state of the three-dimensional negative pressure stimulator 10 according to the manipulation. After a signal sensed through the pressure sensor 234 is inputted to the controller 430, for example, the intensity of the negative pressure is displayed through the display.

Figure 29:
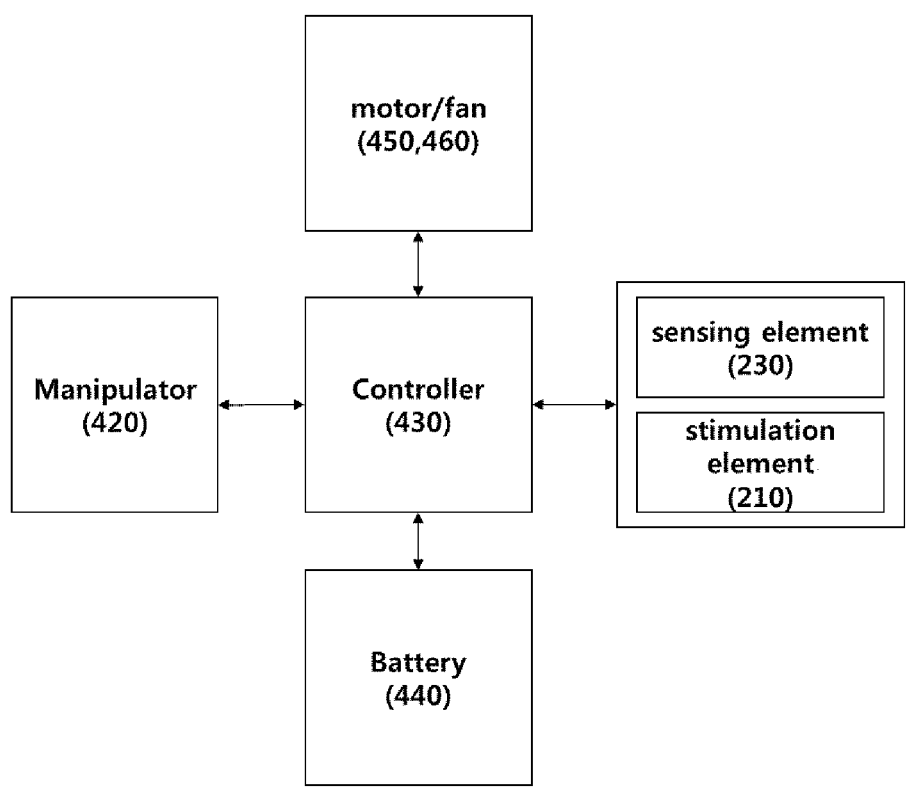
FIG. 29 shows a configuration between a controller and other parts in the three-dimensional negative pressure stimulator according to the present invention.

As shown in FIG. 29, the controller 430 produces control signals corresponding to the manipulations of the manipulator 420, controls the driving of the battery 440, the motor 450, and the fan 460 according to the produced signals, monitors the state of the skin with the signals received from the sensing elements 230 to perform the feedback control, and transmits the control signal to the stimulation elements 210 to allow the composite stimulation to be applied to the skin. Further, the controller 430 controls the display to allow the current skin state or the state of the three-dimensional negative pressure stimulator 10 to be displayed on the display.

If the composite stimulation such as current stimulation, light stimulation, and negative pressure stimulation is applied, for example, the controller 430 is configured as follows. A current controller controls a quantity of current flowing to the electrical stimulation elements 211 and generates a current waveform to apply the current stimulation to the skin. At this time, the quantity of current is micro current capable of offering stimulation to the skin. The current waveform is a square wave, a sine wave, or an arbitrary wave. An LED controller adjusts a quantity of current required for the LED light source. Also, the LED controller controls the currents of the LED light source elements, so that the LED light sources having different wavelength bands maintain the same quantity of light as each other. The LED controller receives data from an ambient light sensor so as to measure the quantity of light of the light source. A negative pressure sensor controls the operations of the driving motor and the fan for absorption. The negative pressure sensor receives the feedback on the value indicating the degree of negative pressure from the pressure sensor.

As described above, according to the present invention, the rearrangements, expansion, and formation stimulation of the skin and subcutaneous tissues, especially, the collagen and elastic fibers are applied three-dimensionally through the first diaphragm of the negative pressure cup, the maximum degree of deformation of the skin and subcutaneous tissues is effectively controlled to apply the negative pressure stimulation stably, the composite stimulation is applied through the stimulation elements located supportedly on the respective diaphragms, and the stimulation customized to the individual's skin state is applied through the sensing elements.

Further, the three-dimensional rearrangements, expansion, and formation stimulation of the skin and subcutaneous tissues are applied through the three-dimensional negative pressure stimulation, and the composite stimulation and the customized stimulation are also provided, thus improving the skin functions.

In addition to the three-dimensional negative pressure stimulation, furthermore, the composite stimulation such as the electrical stimulation and the light stimulation through visible light, infrared ray and ultraviolet ray are transmitted to the large skin contact surface, and the states of localized skin and subcutaneous tissues like skin impedance, temperature, blood flow and so on are sensed, while the state of the negative pressure is being monitored by the pressure sensor, so that in addition to the three-dimensional negative pressure stimulation providing optimized deformation and rearrangements of the skin and subcutaneous tissues, the various composite stimulation is customized to the state of the individual's skin.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A three-dimensional negative pressure composite stimulator assembly configured to perform customized composite stimulation for improvement of skin functions, the stimulator assembly comprising: a motor and fan for generating negative pressure; and a negative pressure cup, wherein the negative pressure cup comprises a housing having a cup shape;
   a first diaphragm located inside the housing; and
   a second diaphragm located above the first diaphragm inside the housing,
   wherein the first diaphragm is configured to come into contact with a target region of a skin or to be placed adjacent thereto,
   wherein the second diaphragm is configured to be spaced apart from the first diaphragm by a distance in a vertical direction in such a manner as to have no contact with the target region of the skin,
   wherein the first diaphragm has a concave shape having a curvature adapted to physically limit a degree of maximum deformation of the target region of the skin by the negative pressure, while an open end of the housing is in tight contact with the skin, so that the skin deformedly protrudes toward a concave side of the first diaphragm,
   wherein the second diaphragm has a concave shape having generally the same curvature as the curvature of the first diaphragm,
   wherein the first diaphragm has at least one first vent formed on a surface thereof in such a manner as to pass air therethrough, and the second diaphragm has at least one second vent formed on a surface thereof in such a manner as to pass air therethrough, wherein the at least one first vent has a concave shape having a curvature on which a ventilation hole is formed,
   wherein the first diaphragm has at least one concave element and at least one convex element disposed thereon to three-dimensionally adjust a deformation of the target region of the skin when the negative pressure is applied,
   wherein the first diaphragm is connected with the housing at the inside of the housing so that the first diaphragm is configured to be adjusted in position vertically to control the degree of maximum deformation of the target region of the skin by the negative pressure, and
   wherein the first diaphragm has an edge area on which at least one stimulation element for stimulating the target region of the skin or at least one sensing element for monitoring a condition of the target region of the skin is located.

2. The three-dimensional negative pressure composite stimulator assembly according to claim 1, wherein air flows from a lower portion of the negative pressure cup toward an upper portion thereof, so that the air inside the negative pressure cup is discharged therethrough to apply the negative pressure to the skin.

3. The three-dimensional negative pressure composite stimulator assembly according to claim 1, wherein the first diaphragm is configured to be separable from the housing so that the first diaphragm is located selectively to block or allow air flows to effectively transmit the negative pressure.

4. The three-dimensional negative pressure composite stimulator assembly according to claim 1, wherein each of the at least one stimulation element is an electrical stimulation element, a light stimulation LED element, or a laser element, and wherein each of the at least one sensing element is a temperature sensor, an impedance sensor, a blood flow sensor, or a pressure sensor.

5. The three-dimensional negative pressure composite stimulator assembly according to claim 1, wherein an amount of the negative pressure is controlled according to time.

6. The three-dimensional negative pressure composite stimulator assembly according to claim 1, wherein the at least one stimulation element is configured to apply both of a temporal three-dimensional stimulation and a spatial three-dimensional stimulation to the target region of the skin.

* * * * *